(12) United States Patent
Chaffee et al.

(10) Patent No.: US 8,700,426 B2
(45) Date of Patent: Apr. 15, 2014

(54) SYSTEMS AND METHODS FOR A NETWORK ANALYZER TOOL

(75) Inventors: Hamilton Chaffee, Vacaville, CA (US); Azita Guzzo, Anaheim Hills, CA (US)

(73) Assignee: StrataCare, LLC, Irvine, CA (US)

( * ) Notice: Subject to any disclaimer, the term of this patent is extended or adjusted under 35 U.S.C. 154(b) by 0 days.

(21) Appl. No.: 13/316,155

(22) Filed: Dec. 9, 2011

(65) Prior Publication Data

US 2013/0151269 A1 Jun. 13, 2013

(51) Int. Cl.
*G06Q 10/00* (2012.01)
*G06Q 50/00* (2012.01)
*G06Q 40/00* (2012.01)

(52) U.S. Cl.
USPC ........................................ 705/2; 705/3; 705/4

(58) Field of Classification Search
USPC .......................................................... 705/2, 3
See application file for complete search history.

(56) References Cited

U.S. PATENT DOCUMENTS

| | | | |
|---|---|---|---|
| 2003/0163349 A1* | 8/2003 | Ho | 705/2 |
| 2006/0053037 A1* | 3/2006 | Kendall et al. | 705/4 |
| 2008/0015892 A1* | 1/2008 | Gowdy et al. | 705/2 |
| 2009/0228301 A1* | 9/2009 | Youngblood et al. | 705/3 |
| 2010/0191547 A1* | 7/2010 | Brandt | 705/4 |

OTHER PUBLICATIONS

Herbert, Gary R., "2009 Health Insurance Market Report," Aug. 17, 2010, State of Utah Insurance Department, p. 4.*
Herbert, Gary R., "2009 Health Insurance Market Report," Aug. 17, 2010, State of Utah.*

* cited by examiner

*Primary Examiner* — Elaine Gort
*Assistant Examiner* — John Go
(74) *Attorney, Agent, or Firm* — Foley & Lardner LLP; Christopher J. McKenna

(57) ABSTRACT

The present solution provides a new tool to assist clients and prospects in evaluating and optimizing their use of PPO networks. The interactive analysis tool of the present solution allows you to rapidly see the impact of different network configurations based on actual experience measured against a comprehensive bill review database.

18 Claims, 13 Drawing Sheets

| | PPOName | Total Charges | BR Allowance | Billed To PPO | PPO Reduction | PPO Discount | Pen ($) | PPO Eff |
|---|---|---|---|---|---|---|---|---|
| Actual | Interplan | 10,657,974 | 3,667,522 | 3,569,695 | 260,019 | 7.28% | 50.84% | 37.04 |
| | No PPO | 8,086,362 | 3,138,960 | 3,049,978 | 0 | 0.00% | 43.44% | 0 |
| | Beech Street Termed | 476,990 | 152,385 | 151,585 | 9,464 | 6.24% | 2.16% | 1.35 |
| | USC Pend And Transmit | 235,577 | 130,043 | 125,208 | 10,147 | 8.10% | 1.78% | 1.45 |
| | Beech Street PPO | 334,548 | 126,760 | 124,304 | 18,601 | 14.96% | 1.77% | 2.65 |
| | Total | 19,791,451 | 7,215,670 | 7,020,770 | 298,231 | 7.51% | 56.56% | 42.48 |
| ProfilerResult (Model of Actual) | Interplan | 12,566,216 | 4,138,997 | 4,038,152 | 283346 | 7.02% | 57.52% | 40.36 |
| | No PPO | 6,102,794 | 2,556,989 | 2,537,778 | 0 | 0.00% | 36.15% | 0 |
| | Beech Street PPO | 1,078,617 | 493,645 | 419,967 | 61,371 | 14.61% | 5.98% | 8.74 |
| | USC Pend And Transmit | 43,824 | 26,039 | 24,873 | 1,835 | 7.38% | 0.35% | 0.26 |
| | Total | 19,791,451 | 7,215,670 | 7,020,770 | 346,552 | 7.73% | 63.85% | 49.36 |
| ProfilerResult | BCC Pend And Transmit | 13,976,895 | 4,950,274 | 4,846,005 | 587,312 | 12.12% | 69.02% | 83.65 |
| | No PPO | 4,273,331 | 1,685,522 | 1,672,077 | 0 | 0.00% | 23.82% | 0 |
| | Interplan | 820,512 | 264,888 | 263,396 | 17,781 | 6.75% | 3.75% | 2.53 |
| | Beech Street PPO | 576,413 | 214,486 | 139,887 | 13163 | 9.41% | 1.99% | 1.87 |
| | IHP | 144300 | 100499 | 99406 | 2291 | 2.30% | 1.42% | 0.33 |
| | Total | 19,791,451 | 7,215,670 | 7,020,770 | 620,547 | 11.60% | 76.18% | 88.39 |
| ProfilerResult | First Health Pend And Transmit | 15,286,214 | 5,457,999 | 5,277,605 | 504,652 | 9.56% | 75.17% | 71.88 |
| | No PPO | 4,451,886 | 1,734,025 | 1,720,028 | 0 | 0.00% | 24.50% | 0 |
| | IHP | 40,081 | 18,577 | 18,068 | 946 | 5.24% | 0.26% | 0.13 |
| | Beech Street PPO | 12,300 | 4,714 | 4,714 | 434 | 9.20% | 0.07% | 0.06 |
| | Interplan | 970 | 355 | 355 | 52 | 14.66% | 0.01% | 0.01 |
| | Total | 19,791,451 | 7,215,670 | 7,020,770 | 506,084 | 9.55% | 75.50% | 72.08 |
| ProfilerResult | Corvel Pend And Transmit | 14,935,350 | 5,311,505 | 5,133,995 | 488,273 | 9.51% | 73.13% | 69.55 |
| | No PPO | 4,770,949 | 1,861,763 | 1,848,127 | 0 | 0.00% | 26.32% | 0 |
| | IHP | 34,627 | 22,147 | 20,355 | 1691 | 8.31% | 0.29% | 0.24 |
| | Beech Street PPO | 32,020 | 14,120 | 13,650 | 1,197 | 8.77% | 0.19% | 0.17 |
| | Interplan | 18,506 | 6,135 | 4,643 | 477 | 10.26% | 0.07% | 0.07 |
| | Total | 19,791,451 | 7,215,670 | 7,020,770 | 491,638 | 9.50% | 73.68% | 70.03 |

Report Type: StrataCare
Account Level1: *All
Client: *
From: 1/1/2011
Exclude Service Class: NOTHING
Second Network: No PPO
Forth Network: No PPO Customer: TEST
Account Level2: *All
State: California
To: 6/30/2011
Primary Network: First Health Pend And Transmit
Third Network: No PPO

PPO Analysis for TEST State of CA from 1/1/2011 to 6/30/2011

When PPO1: First Health Pend And Transmit | PPO2: No PPO | PPO3: No PPO | PPO4: No PPO Excluding Service Classes: NOTHING (PBM data always excluded)

AccountGroup: *All|*All
Client : 0

| | PPO | PPOName | Bill Count | Total Charges | BR Allowance | Billed To PPO | Pen ($) | PPO Discount | PPO Reduction | PPO Eff |
|---|---|---|---|---|---|---|---|---|---|---|
| Actual | 0-38-1 | First Health Pend And Transmit | 624 | 337,358 | 147,053 | 140,873 | 58.97 % | 8.65 % | 12,182 | 50.99 |
| | -1 | No PPO | 203 | 206,577 | 103,746 | 98,022 | 41.03 % | 0.00 % | 0 | 0.00 |
| | | Total | 827 | 543,935 | 250,799 | 238,895 | 58.97 % | 8.65 % | 12,182 | 50.99 |
| ProfilerResult | 0-38-1 | First Health Pend And Transmit | 686 | 401,109 | 187,776 | 177,191 | 74.17 % | 8.11 % | 14,372 | 60.16 |
| | -1 | No PPO | 141 | 142,826 | 63,023 | 61,704 | 25.83 % | 0.00 % | 0 | 0.00 |
| | | Total | 827 | 543,935 | 250,799 | 238,895 | 74.17 % | 8.11 % | 14,372 | 60.16 |

⊞ Model Detail:

⊞ Actual Detail:

⊞ Other:

*Fig. 3A*

PPO Analysis for TEST State of CA from 1/1/2011 to 6/30/2011

When PPO1: First Health Pend And Transmit \ PPO2: No PPO \ PPO3: No PPO \ PPO4: No PPO
Excluding Service Classes: NOTHING (PBM data always excluded)
AccountGroup: *All\*All
Client : 0

|  | PPO | PPOName | Bill Count | Total Charges | BR Allowance | Billed To PPO | Pen ($) | PPO Discount | PPO Reduction | PPO Eff |
|---|---|---|---|---|---|---|---|---|---|---|
| Actual | 0-36-1 | First Health Pend And Transmit | 624 | 337,358 | 147,053 | 140,873 | 58.97 % | 8.65 % | 12,182 | 50.99 |
|  | -1 | No PPO | 203 | 206,577 | 103,746 | 98,022 | 41.03 % | 0.00 % | 0 | 0.00 |
|  |  | Total | 827 | 543,935 | 250,799 | 238,895 | 58.97 % | 8.65 % | 12,182 | 50.99 |
| ProfilerResult | 0-36-1 | First Health Pend And Transmit | 686 | 401,109 | 187,776 | 177,191 | 74.17 % | 8.11 % | 14,372 | 60.16 |
|  | -1 | No PPO | 141 | 142,826 | 63,023 | 61,704 | 25.83 % | 0.00 % | 0 | 0.00 |
|  |  | Total | 827 | 543,935 | 250,799 | 238,895 | 74.17 % | 8.11 % | 14,372 | 60.16 |

⊟ Model Detail:
⊞ By PPO\ServiceClass\TaxID:
⊞ By PPO\TaxID:
⊞ By ServiceClass\PPO\TaxID:

⊟ Actual Detail:
⊞ By PPO\ServiceClass\TaxID:
⊞ By PPO\TaxID:
⊞ By ServiceClass\PPO\TaxID:

⊟ Other:
⊞ Pricing Hierarchy Match:
⊞ PPO TaxID count in state:
⊞ Model vs. Actual:
⊞ PPO Configuration:

PPO Analysis for TEST State of CA from 1/1/2011 to 6/30/2011

When PPO1: First Health Pend And Transmit \ PPO2: No PPO \ PPO3: No PPO \ PPO4: No PPO Excluding Service Classes: NOTHING (PBM data always excluded)

AccountGroup: *All\*All

Client : 0

| | PPO | PPOName | Bill Count | Total Charges | BR Allowance | Billed To PPO | Pen ($) | PPO Discount | PPO Reduction | PPO Eff |
|---|---|---|---|---|---|---|---|---|---|---|
| Actual | 0-38-1 | First Health Pend And Transmit | 624 | 337,358 | 147,053 | 140,873 | 58.97 % | 8.65 % | 12,182 | 50.99 |
| | -1 | No PPO | 203 | 206,577 | 103,746 | 98,022 | 41.03 % | 0.00 % | 0 | 0.00 |
| | | Total | 827 | 543,935 | 250,799 | 238,895 | 58.97 % | 8.66 % | 12,182 | 50.99 |
| ProfilerResult | 0-38-1 | First Health Pend And Transmit | 686 | 401,109 | 187,776 | 177,191 | 74.17 % | 8.11 % | 14,372 | 60.16 |
| | -1 | No PPO | 141 | 142,826 | 63,023 | 61,704 | 25.83 % | 0.00 % | 0 | 0.00 |
| | | Total | 827 | 543,935 | 250,799 | 238,895 | 74.17 % | 8.11 % | 14,372 | 60.16 |

⊞ Model Detail:

⊞ By PPO\ServiceClass\TaxID:

⊞ By PPO\TaxID:

⊞ By ServiceClass\PPO\TaxID:

⊟ Actual Detail:

⊞ By PPO\ServiceClass\TaxID:

⊞ By PPO\TaxID:

⊞ By ServiceClass\PPO\TaxID:

⊟ Other:

⊟ Pricing Hierarchy Match:

| Pricing Hierarchy Match | BilledToPPO | % of Total |
|---|---|---|
| State-Net-ServiceClass-TaxID | 175,925 | 99.29 % |
| State-Net-ServiceClass | 1,266 | 0.71 % |
| Total | 177,191 | |

⊞ PPO TaxID count in state:

⊞ Model vs. Actual:

⊞ PPO Configuration:

PPO Analysis for TEST State of CA from 1/1/2011 to 6/30/2011

When PPO1: BCC Pend And Transmit \ PPO2: IHP \ PPO3: PrimeHealth \ PPO4: No PPO
Excluding Service Classes: NOTHING (PBM data always excluded)
AccountGroup: *All\*All
Client : 0

| | PPO | PPOName | Bill Count | Total Charges | BR Allowance | Billed To PPO | Pen ($) | PPO Discount | PPO Reduction | PPO Eff |
|---|---|---|---|---|---|---|---|---|---|---|
| Actual | 0-38-1 | First Health Pend And Transmit | 624 | 337,358 | 147,053 | 140,873 | 58.97 % | 8.65 % | 12,182 | 50.99 |
| | -1 | No PPO | 203 | 206,577 | 103,746 | 98,022 | 41.03 % | 0.00 % | 0 | 0.00 |
| | | Total | 827 | 543,935 | 250,799 | 238,895 | 58.97 % | 8.65 % | 12,182 | 50.99 |
| ProfilerResult | 0-32-1 | BCC Pend And Transmit | 653 | 380,982 | 176,221 | 172,012 | 72.00 % | 9.50 % | 16,335 | 68.38 |
| | | No PPO | 126 | 123,624 | 49,753 | 48,434 | 20.27 % | 0.00 % | 0 | 0.00 |
| | 0-52-1 | IHP | 37 | 32,691 | 21,109 | 14,733 | 6.17 % | 4.57 % | 673 | 2.82 |
| | 0-42-1 | PrimeHealth | 11 | 6,638 | 3,715 | 3,715 | 1.56 % | 13.82 % | 514 | 2.15 |
| | | Total | 827 | 543,935 | 250,799 | 238,895 | 79.73 % | 9.20 % | 17,521 | 73.34 |

⊞ Model Detail:

⊞ Actual Detail:

⊞ Other:

*Fig. 3G*

SYSTEMS AND METHODS FOR A NETWORK ANALYZER TOOL

A portion of the disclosure of this patent document contains material which is subject to copyright protection. The copyright owner has no objection to the facsimile reproduction by anyone of the patent document or the patent disclosure, as it appears in the file or records of the Patent and Trademark Office, but otherwise reserves all copyright rights whatsoever.

FIELD OF THE DISCLOSURE

This disclosure generally relates to systems and methods for a health care provider network optimization tool. In particular, this disclosure relates to systems and methods.

BACKGROUND OF THE DISCLOSURE

Companies typically provide insurance options for their employees, such as workers' compensation or health care insurance. In some cases, a company may self-insure, and in other cases the company may use a third-party insurance company. In an effort to reduce medical costs, an insurance company may offer one or more preferred provider organizations ("PPO"). A PPO may comprise medical doctors, hospitals, and other health care providers who have contracted with an insurer or a third-party administrator to provide health care services at reduced rates to clients of the insurer or third-party administrator. A health care provider may be associated with one or more PPOs. An insured may receive a discount for a medical service by selecting a participating health care provider. PPOs may be confined to one or more states or geographic regions, and may also contract with other PPOs. PPO administrators may use their bargaining power to negotiate a plurality of favorable terms with participating health care providers. As a result, PPOs may provide members with a discount below the regularly charged rates of the participating health care provider.

Discounts provided by each PPO may vary based on the size of the network, its location, medical services, efficiency, etc. Furthermore, a client may realize more or less discounts based on the types of services rendered to the insured via the PPO, the discounts on those services, etc. Due to the abundance of diverse PPOs, it is a challenge for a client or insurance company to accurately determine which PPO or group of PPOs will provide them with optimum benefits.

BRIEF SUMMARY OF THE DISCLOSURE

The present solution provide a new interactive analysis tool to assist clients and prospects in evaluating and optimizing their use of PPO networks. This interactive analysis tool allows a user to rapidly see the impact of different PPO network configurations based on actual experience measured against a comprehensive bill review database. Key benefits of this tool include, but are not limited to:

- Multiple networks and stacking orders can be evaluated quickly and easily using a single tool.
- Each network is evaluated objectively using the same criteria, eliminating the biases and inconsistencies when networks do their own analysis.
- Savings are calculated at the service level for each provider for each network for each jurisdiction rather than just using network averages.

This savings calculation is not only more accurate, it also allows the user to drill down into the data and see exactly where the savings are coming from.

In some aspects, the present solution is directed to a method for evaluating efficiency of billing of services via a health care provider network. The method includes receiving, by a tool executing on a device, a first selection of a healthcare provider network from multiple choices of health care provider networks. The method includes receiving, by the tool, a second selection of a state for which services were provided by the selected health care provider network and determining, by the tool via a database of reviewed bill data, a penetration and a savings for bills on services within the state for the selected health care provider network.

In some embodiments, the method includes receiving, by the tool, the selection of the healthcare provider network comprising a preferred provider organization (PPO). In some embodiments, the method includes receiving, by the tool, identification of a time period for determining the penetration efficiency and savings. In some embodiments, the method includes determining the penetration efficiency and the savings for bills on service within the state for the selected health care provider network during the time period. In some embodiments, the method includes receiving, by the tool, the second selection of the state from a plurality of states in which the healthcare provider network provides services. In some embodiments, the method includes receiving, by the tool, a third selection of a second health care provider network. In some embodiments, the method includes determining, by the tool, the penetration and the savings for bills on service within the state for the health care provider network and the second health care provider network.

In some embodiments, the method includes determining, by the tool, the penetration as a total of bill reviewed charges allowed for a client of the selected health care provider network divided by a total of bill reviewed charges allowed for a client for a plurality of health care provider networks. In some embodiments, the method includes determining, by the tool, the savings as a discount of the selected health care provider applied to a total amount saved from bill review of charges for the selected health care provider network. In some embodiments, the method includes determining, by the tool, the penetration and the savings on a per service class basis for the selected health care provider network. In some embodiments, the method includes determining, by the tool, the penetration and the savings on a per service class basis for the selected health care provider network and excluding one or more service classes selected from a plurality of service classes. In some embodiments, the method includes determining, by the tool, a network efficiency based on the penetration and the savings.

In some aspects, the present solution is directed to a method for evaluating efficiency of selectable health care providers from a plurality of healthcare provider networks. The method includes receiving, by a tool executing on a device, a first selection of a first healthcare provider network of a plurality of healthcare provider networks. The method also includes receiving, by the tool, a second selection of a second healthcare provider network of a plurality of healthcare provider networks; and providing, by the tool, a comparison of efficiency of billing of services between the first health care provider network and the second healthcare provider network.

In some embodiments, the method includes receiving, by the tool, a selection of a state from a plurality of states in which the first healthcare provider network provided services. In some embodiments, the method includes receiving, by the tool, identification of a time period for the comparison. In some embodiments, the method includes receiving, by the tool, the second selection of the second healthcare provider network of the plurality of healthcare provider networks for a same state as the first the first healthcare provider network. In some embodiments, the method includes determining, by the tool from the database of reviewed bills, for each of the first healthcare provider network and the second healthcare provider network a network penetration and a network savings based on charges allowed via bill review. In some embodiments, the method includes determining, by the tool from the database of reviewed bills, for each of the first healthcare provider network and the second healthcare provider network a network efficiency from a corresponding network penetration and a network savings based on charges allowed via bill review. In some embodiments, the method includes receiving, by the tool, a selection of a client from a plurality of clients. In some embodiments, the method includes determining, by the tool from the database of reviewed bills, the comparison of efficiency of billing of services for the selected client between the first health care provider network and the second healthcare provider network.

BRIEF DESCRIPTION OF THE DRAWINGS

The foregoing and other objects, aspects, features, and advantages of the disclosure will become more apparent and better understood by referring to the following description taken in conjunction with the accompanying drawings, in which:

FIG. 2C is a diagram of an embodiment of results and/or output from a network analyzer; and FIG. 3A-G contains illustrations of systems and methods of a network analyzer.

DETAILED DESCRIPTION

Figure 1A:
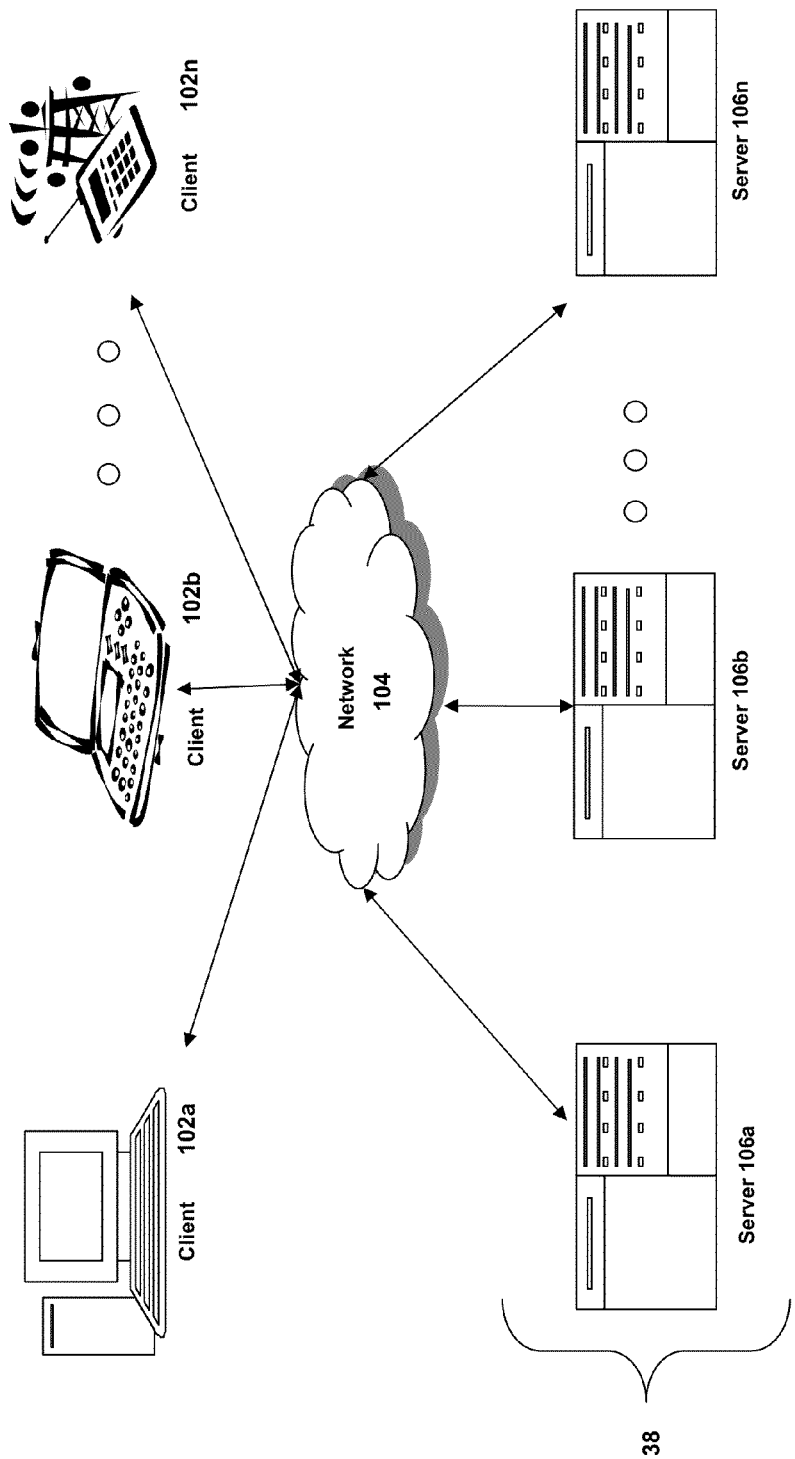
FIG. 1A is a block diagram depicting an embodiment of a network environment comprising client device in communication with server device.

For purposes of reading the description of the various embodiments below, the following descriptions of the sections of the specification and their respective contents may be helpful:
Section A describes a network environment and computing environment which may be useful for practicing embodiments described herein; and
Section B describes embodiments of systems and methods for a network analyzer.
A. Computing and Network Environment Prior to discussing specific embodiments of the present solution, it may be helpful to describe aspects of the operating environment as well as associated system components (e.g., hardware elements) in connection with the methods and systems described herein. Referring to FIG. 1A, an embodiment of a network environment is depicted. In brief overview, the network environment includes one or more clients 102a-102n (also generally referred to as local machine(s) 102, client(s) 102, client node(s) 102, client machine(s) 102, client computer(s) 102, client device(s) 102, endpoint(s) 102, or endpoint node(s) 102) in communication with one or more servers 106a-106n (also generally referred to as server(s) 106, node 106, or remote machine(s) 106) via one or more networks 104. In some embodiments, a client 102 has the capacity to function as both a client node seeking access to resources provided by a server and as a server providing access to hosted resources for other clients 102a-102n.

Although FIG. 1A shows a network 104 between the clients 102 and the servers 106, the clients 102 and the servers 106 may be on the same network 104. The network 104 can be a local-area network (LAN), such as a company Intranet, a metropolitan area network (MAN), or a wide area network (WAN), such as the Internet or the World Wide Web. In some embodiments, there are multiple networks 104 between the clients 102 and the servers 106. In one of these embodiments, a network 104' (not shown) may be a private network and a network 104 may be a public network. In another of these embodiments, a network 104 may be a private network and a network 104' a public network. In still another of these embodiments, networks 104 and 104' may both be private networks.

The network 104 may be any type and/or form of network and may include any of the following: a point-to-point network, a broadcast network, a wide area network, a local area network, a telecommunications network, a data communication network, a computer network, an ATM (Asynchronous Transfer Mode) network, a SONET (Synchronous Optical Network) network, a SDH (Synchronous Digital Hierarchy) network, a wireless network and a wireline network. In some embodiments, the network 104 may comprise a wireless link, such as an infrared channel or satellite band. The topology of the network 104 may be a bus, star, or ring network topology. The network 104 may be of any such network topology as known to those ordinarily skilled in the art capable of supporting the operations described herein. The network may comprise mobile telephone networks utilizing any protocol or protocols used to communicate among mobile devices, including AMPS, TDMA, CDMA, GSM, GPRS or UMTS. In some embodiments, different types of data may be transmitted via different protocols. In other embodiments, the same types of data may be transmitted via different protocols.

In some embodiments, the system may include multiple, logically-grouped servers 106. In one of these embodiments, the logical group of servers may be referred to as a server farm 38 or a machine farm 38. In another of these embodiments, the servers 106 may be geographically dispersed. In other embodiments, a machine farm 38 may be administered as a single entity. In still other embodiments, the machine farm 38 includes a plurality of machine farms 38. The servers 106 within each machine farm 38 can be heterogeneous—one or more of the servers 106 or machines 106 can operate according to one type of operating system platform (e.g., WINDOWS NT, manufactured by Microsoft Corp. of Redmond, Wash.), while one or more of the other servers 106 can operate on according to another type of operating system platform (e.g., Unix or Linux).

In one embodiment, servers 106 in the machine farm 38 may be stored in high-density rack systems, along with associated storage systems, and located in an enterprise data center. In this embodiment, consolidating the servers 106 in this way may improve system manageability, data security, the physical security of the system, and system performance by locating servers 106 and high performance storage systems on localized high performance networks. Centralizing the servers 106 and storage systems and coupling them with advanced system management tools allows more efficient use of server resources.

The servers 106 of each machine farm 38 do not need to be physically proximate to another server 106 in the same machine farm 38. Thus, the group of servers 106 logically grouped as a machine farm 38 may be interconnected using a wide-area network (WAN) connection or a metropolitan-area network (MAN) connection. For example, a machine farm 38 may include servers 106 physically located in different continents or different regions of a continent, country, state, city, campus, or room. Data transmission speeds between servers 106 in the machine farm 38 can be increased if the servers 106 are connected using a local-area network (LAN) connection or some form of direct connection. Additionally, a heterogeneous machine farm 38 may include one or more servers 106 operating according to a type of operating system, while one or more other servers 106 execute one or more types of hypervisors rather than operating systems. In these embodiments, hypervisors may be used to emulate virtual hardware, partition physical hardware, virtualize physical hardware, and execute virtual machines that provide access to computing environments. Hypervisors may include those manufactured by VMWare, Inc., of Palo Alto, Calif.; the Xen hypervisor, an open source product whose development is overseen by Citrix Systems, Inc.; the VirtualServer or virtual PC hypervisors provided by Microsoft or others.

Management of the machine farm 38 may be de-centralized. For example, one or more servers 106 may comprise components, subsystems and modules to support one or more management services for the machine farm 38. In one of these embodiments, one or more servers 106 provide functionality for management of dynamic data, including techniques for handling failover, data replication, and increasing the robustness of the machine farm 38. Each server 106 may communicate with a persistent store and, in some embodiments, with a dynamic store.

Server 106 may be a file server, application server, web server, proxy server, appliance, network appliance, gateway, gateway, gateway server, virtualization server, deployment server, SSL VPN server, or firewall. In one embodiment, the server 106 may be referred to as a remote machine or a node. In another embodiment, a plurality of nodes 290 may be in the path between any two communicating servers.

Figure 1B:
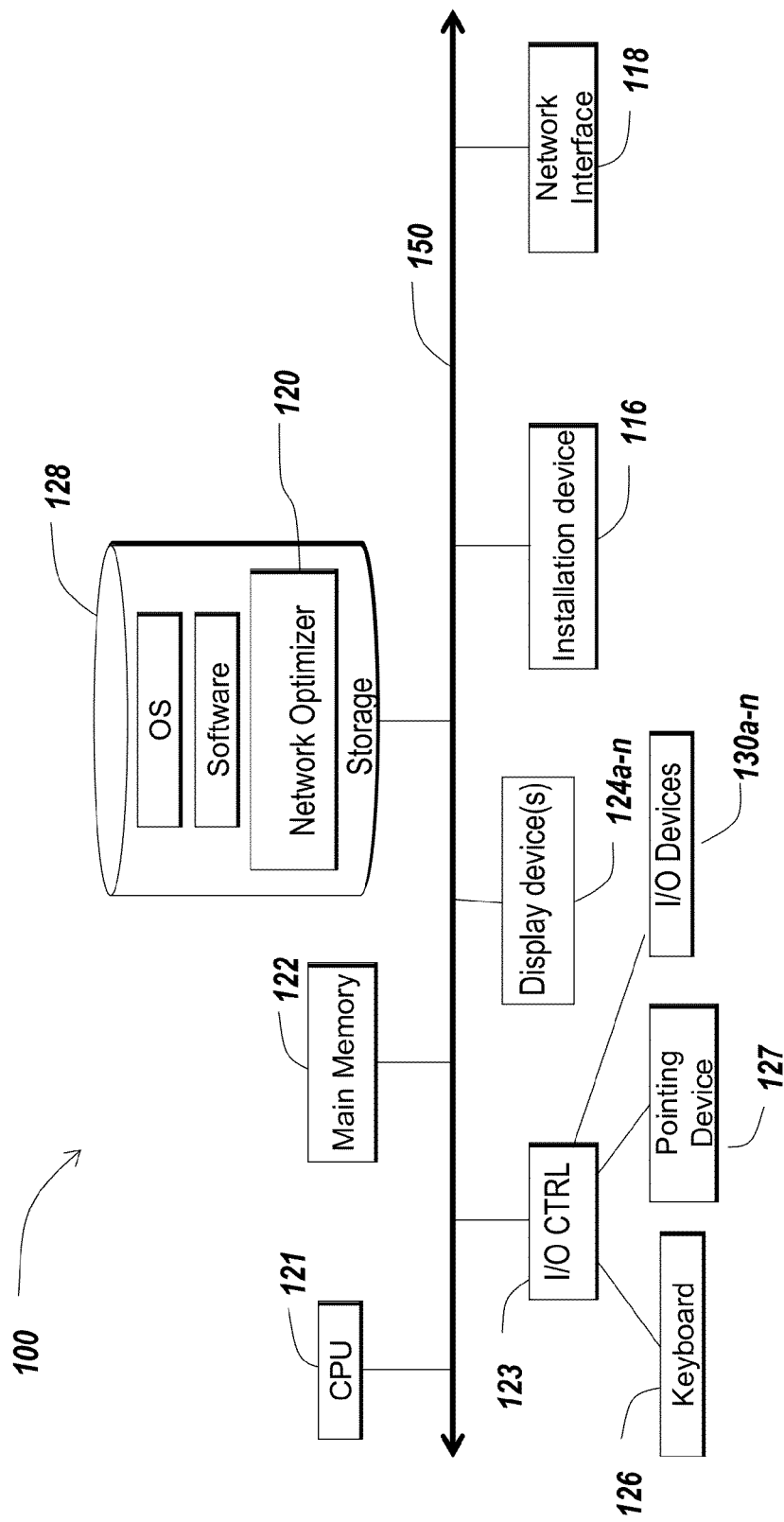
FIGS. 1B and 1C are block diagrams depicting embodiments of computing devices useful in connection with the methods and systems described herein.
Figure 1C:
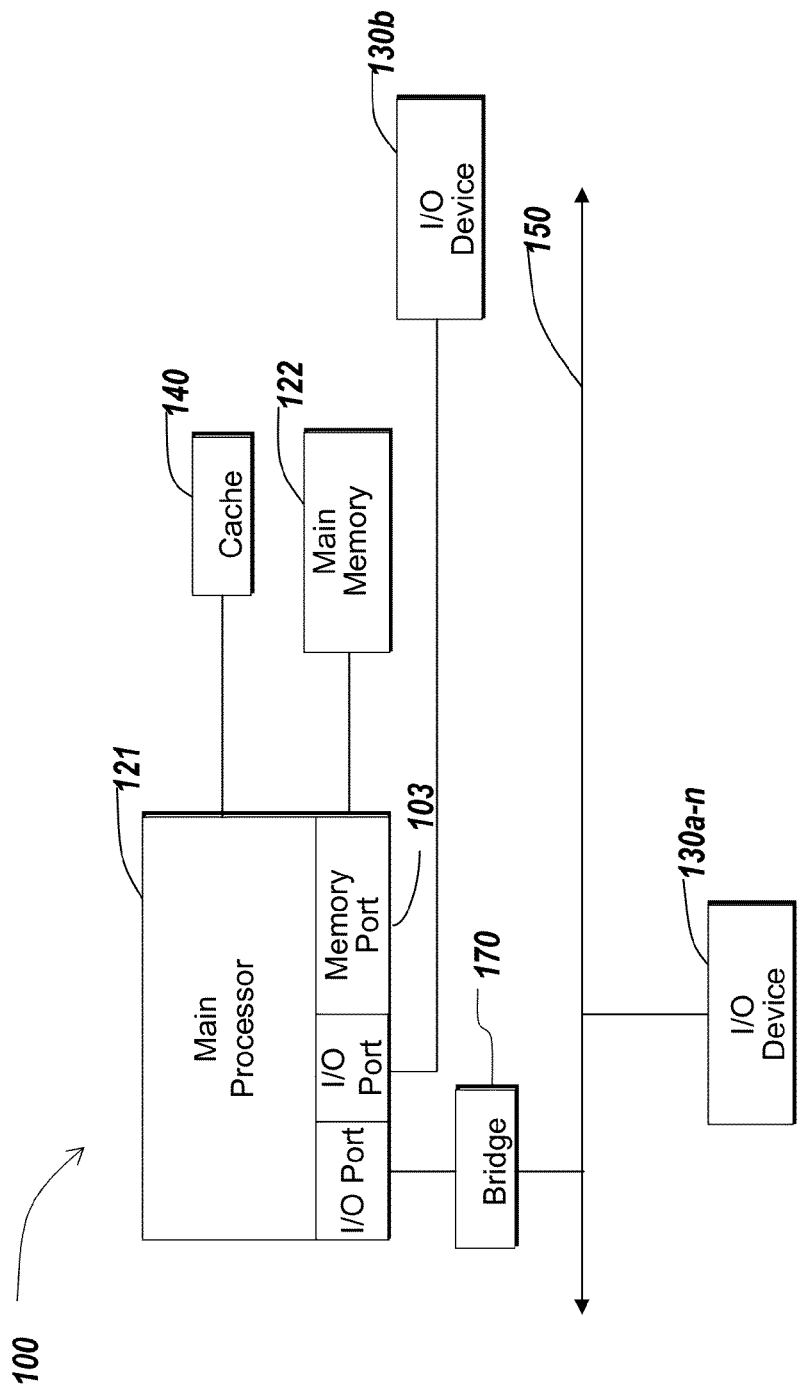

The client 102 and server 106 may be deployed as and/or executed on any type and form of computing device, such as a computer, network device or appliance capable of communicating on any type and form of network and performing the operations described herein. FIGS. 1B and 1C depict block diagrams of a computing device 100 useful for practicing an embodiment of the client 102 or a server 106. As shown in FIGS. 1B and 1C, each computing device 100 includes a central processing unit 121, and a main memory unit 122. As shown in FIG. 1B, a computing device 100 may include a storage device 128, an installation device 116, a network interface 118, an I/O controller 123, display devices 124a-102n, a keyboard 126 and a pointing device 127, such as a mouse. The storage device 128 may include, without limitation, an operating system, software, and a software of a network analyzer 120. As shown in FIG. 1C, each computing device 100 may also include additional optional elements, such as a memory port 103, a bridge 170, one or more input/output devices 130a-130n (generally referred to using reference numeral 130), and a cache memory 140 in communication with the central processing unit 121.

The central processing unit 121 is any logic circuitry that responds to and processes instructions fetched from the main memory unit 122. In many embodiments, the central processing unit 121 is provided by a microprocessor unit, such as: those manufactured by Intel Corporation of Mountain View, Calif.; those manufactured by Motorola Corporation of Schaumburg, Ill.; those manufactured by Transmeta Corporation of Santa Clara, Calif.; the RS/6000 processor, those manufactured by International Business Machines of White Plains, N.Y.; or those manufactured by Advanced Micro Devices of Sunnyvale, Calif. The computing device 100 may be based on any of these processors, or any other processor capable of operating as described herein.

Main memory unit 122 may be one or more memory chips capable of storing data and allowing any storage location to be directly accessed by the microprocessor 121, such as Static random access memory (SRAM), Burst SRAM or Synch-Burst SRAM (BSRAM), Dynamic random access memory (DRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Enhanced DRAM (EDRAM), synchronous DRAM (SDRAM), JEDEC SRAM, PC 100 SDRAM, Double Data Rate SDRAM (DDR SDRAM), Enhanced SDRAM (ESDRAM), SyncLink DRAM (SLDRAM), Direct Rambus DRAM (DRDRAM), or Ferroelectric RAM (FRAM). The main memory 122 may be based on any of the above described memory chips, or any other available memory chips capable of operating as described herein. In the embodiment shown in FIG. 1B, the processor 121 communicates with main memory 122 via a system bus 150 (described in more detail below). FIG. 1C depicts an embodiment of a computing device 100 in which the processor communicates directly with main memory 122 via a memory port 103. For example, in FIG. 1C the main memory 122 may be DRDRAM.

FIG. 1C depicts an embodiment in which the main processor 121 communicates directly with cache memory 140 via a secondary bus, sometimes referred to as a backside bus. In other embodiments, the main processor 121 communicates with cache memory 140 using the system bus 150. Cache memory 140 typically has a faster response time than main memory 122 and is typically provided by SRAM, BSRAM, or EDRAM. In the embodiment shown in FIG. 1C, the processor 121 communicates with various I/O devices 130 via a local system bus 150. Various buses may be used to connect the central processing unit 121 to any of the I/O devices 130, including a VESA VL bus, an ISA bus, an EISA bus, a MicroChannel Architecture (MCA) bus, a PCI bus, a PCI-X bus, a PCI-Express bus, or a NuBus. For embodiments in which the I/O device is a video display 124, the processor 121 may use an Advanced Graphics Port (AGP) to communicate with the display 124. FIG. 1C depicts an embodiment of a computer 100 in which the main processor 121 communicates directly with I/O device 130b via HYPERTRANSPORT, RAPIDIO, or INFINIBAND communications technology. FIG. 1C also depicts an embodiment in which local busses and direct communication are mixed: the processor 121 communicates with I/O device 130a using a local interconnect bus while communicating with I/O device 130b directly.

A wide variety of I/O devices 130a-130n may be present in the computing device 100. Input devices include keyboards, mice, trackpads, trackballs, microphones, dials, and drawing tablets. Output devices include video displays, speakers, inkjet printers, laser printers, and dye-sublimation printers. The I/O devices may be controlled by an I/O controller 123 as shown in FIG. 1B. The I/O controller may control one or more I/O devices such as a keyboard 126 and a pointing device 127, e.g., a mouse or optical pen. Furthermore, an I/O device may also provide storage and/or an installation medium 116 for the computing device 100. In still other embodiments, the computing device 100 may provide USB connections (not shown) to receive handheld USB storage devices such as the USB Flash Drive line of devices manufactured by Twintech Industry, Inc. of Los Alamitos, Calif.

Referring again to FIG. 1B, the computing device 100 may support any suitable installation device 116, such as a floppy disk drive for receiving floppy disks such as 3.5-inch, 5.25-inch disks or ZIP disks, a CD-ROM drive, a CD-R/RW drive, a DVD-ROM drive, a flash memory drive, tape drives of various formats, USB device, hard-drive or any other device suitable for installing software and programs. The computing device 100 may further comprise a storage device, such as one or more hard disk drives or redundant arrays of independent disks, for storing an operating system and other related software, and for storing application software programs such as any program related to the software 120 for the network analyzer. Optionally, any of the installation devices 116 could also be used as the storage device. Additionally, the operating system and the software can be run from a bootable medium, for example, a bootable CD, such as KNOPPIX, a bootable CD for GNU/Linux that is available as a GNU/Linux distribution from knoppix.net.

Furthermore, the computing device 100 may include a network interface 118 to interface to the network 104 through a variety of connections including, but not limited to, standard telephone lines, LAN or WAN links (e.g., 802.11, T1, T3, 56 kb, X.25, SNA, DECNET), broadband connections (e.g., ISDN, Frame Relay, ATM, Gigabit Ethernet, Ethernet-over-SONET), wireless connections, or some combination of any or all of the above. Connections can be established using a variety of communication protocols (e.g., TCP/IP, IPX, SPX, NetBIOS, Ethernet, ARCNET, SONET, SDH, Fiber Distributed Data Interface (FDDI), RS232, IEEE 802.11, IEEE 802.11a, IEEE 802.11b, IEEE 802.11g, CDMA, GSM, WiMax and direct asynchronous connections). In one embodiment, the computing device 100 communicates with other computing devices 100' via any type and/or form of gateway or tunneling protocol such as Secure Socket Layer (SSL) or Transport Layer Security (TLS), or the Citrix Gateway Protocol manufactured by Citrix Systems, Inc. of Ft. Lauderdale, Fla. The network interface 118 may comprise a built-in network adapter, network interface card, PCMCIA network card, card bus network adapter, wireless network adapter, USB network adapter, modem or any other device suitable for interfacing the computing device 100 to any type of network capable of communication and performing the operations described herein.

In some embodiments, the computing device 100 may comprise or be connected to multiple display devices 124a-124n, which each may be of the same or different type and/or form. As such, any of the I/O devices 130a-130n and/or the I/O controller 123 may comprise any type and/or form of suitable hardware, software, or combination of hardware and software to support, enable or provide for the connection and use of multiple display devices 124a-124n by the computing device 100. For example, the computing device 100 may include any type and/or form of video adapter, video card, driver, and/or library to interface, communicate, connect or otherwise use the display devices 124a-124n. In one embodiment, a video adapter may comprise multiple connectors to interface to multiple display devices 124a-124n. In other embodiments, the computing device 100 may include multiple video adapters, with each video adapter connected to one or more of the display devices 124a-124n. In some embodiments, any portion of the operating system of the computing device 100 may be configured for using multiple displays 124a-124n. In other embodiments, one or more of the display devices 124a-124n may be provided by one or more other computing devices, such as computing devices 100a and 100b connected to the computing device 100, for example, via a network. These embodiments may include any type of software designed and constructed to use another computer's display device as a second display device 124a for the computing device 100. One ordinarily skilled in the art will recognize and appreciate the various ways and embodiments that a computing device 100 may be configured to have multiple display devices 124a-124n.

In further embodiments, an I/O device 130 may be a bridge between the system bus 150 and an external communication bus, such as a USB bus, an Apple Desktop Bus, an RS-232 serial connection, a SCSI bus, a FireWire bus, a FireWire 800 bus, an Ethernet bus, an AppleTalk bus, a Gigabit Ethernet bus, an Asynchronous Transfer Mode bus, a HIPPI bus, a Super HIPPI bus, a SerialPlus bus, a SCI/LAMP bus, a FibreChannel bus, a Serial Attached small computer system interface bus, or a HDMI bus.

A computing device 100 of the sort depicted in FIGS. 1B and 1C typically operates under the control of operating systems, which control scheduling of tasks and access to system resources. The computing device 100 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 3.x, WINDOWS 95, WINDOWS 98, WINDOWS 2000, WINDOWS NT 3.51, WINDOWS NT 4.0, WINDOWS CE, WINDOWS MOBILE, WINDOWS XP, WINDOWS VISTA, and WINDOWS 7, all of which are manufactured by Microsoft Corporation of Redmond, Wash.; MAC OS, manufactured by Apple Computer of Cupertino, Calif.; OS/2, manufactured by International Business Machines of Armonk, N.Y.; and Linux, a freely-available operating system distributed by Caldera Corp. of Salt Lake City, Utah, or any type and/or form of a Unix operating system, among others.

The computer system 100 can be any workstation, telephone, desktop computer, laptop or notebook computer, server, handheld computer, mobile telephone or other portable telecommunications device, media playing device, a gaming system, mobile computing device, or any other type and/or form of computing, telecommunications or media device that is capable of communication. The computer system 100 has sufficient processor power and memory capacity to perform the operations described herein. For example, the computer system 100 may comprise a device of the IPOD, IPHONE, or APPLE TV family of devices manufactured by Apple Computer of Cupertino, Calif., a PLAYSTATION 2, PLAYSTATION 3, or PERSONAL PLAYSTATION PORTABLE (PSP) device manufactured by the Sony Corporation of Tokyo, Japan, a NINTENDO DS, NINTENDO GAMEBOY, NINTENDO GAMEBOY ADVANCED, NINTENDO REVOLUTION, or a NINTENDO WII device manufactured by Nintendo Co., Ltd., of Kyoto, Japan, an XBOX or XBOX 360 device manufactured by the Microsoft Corporation of Redmond, Wash.

In some embodiments, the computing device 100 may have different processors, operating systems, and input devices consistent with the device. For example, in one embodiment, the computing device 100 is a TREO 180, 270, 600, 650, 680, 700p, 700w, or 750 smart phone manufactured by Palm, Inc. In some of these embodiments, the TREO smart phone is operated under the control of the PalmOS operating system and includes a stylus input device as well as a five-way navigator device.

In other embodiments the computing device 100 is a mobile device, such as a JAVA-enabled cellular telephone or personal digital assistant (PDA), such as the i55sr, i58sr, i85s, i88s, i90c, i95cl, or the im1100, all of which are manufactured by Motorola Corp. of Schaumburg, Ill., the 6035 or the 7135, manufactured by Kyocera of Kyoto, Japan, or the i300 or i330, manufactured by Samsung Electronics Co., Ltd., of Seoul, Korea. In some embodiments, the computing device 100 is a mobile device manufactured by Nokia of Finland, or by Sony Ericsson Mobile Communications AB of Lund, Sweden.

In still other embodiments, the computing device 100 is a Blackberry handheld or smart phone, such as the devices manufactured by Research In Motion Limited, including the Blackberry 7100 series, 8700 series, 7700 series, 7200 series, the Blackberry 7520, or the Blackberry Pearl 8100. In yet other embodiments, the computing device 100 is a smart phone, Pocket PC, Pocket PC Phone, or other handheld mobile device supporting Microsoft Windows Mobile Software. Moreover, the computing device 100 can be any workstation, desktop computer, laptop or notebook computer, server, handheld computer, mobile telephone, any other computer, or other form of computing or telecommunications device that is capable of communication and that has sufficient processor power and memory capacity to perform the operations described herein.

In some embodiments, the computing device 100 is a digital audio player. In one of these embodiments, the computing device 100 is a digital audio player such as the Apple IPOD, IPOD Touch, and IPOD NANO lines of devices, manufactured by Apple Computer of Cupertino, Calif. In another of these embodiments, the digital audio player may function as both a portable media player and as a mass storage device. In other embodiments, the computing device 100 is a digital audio player such as the DigitalAudimpression opportunity layer Select MP3 players, manufactured by Samsung Electronics America, of Ridgefield Park, N.J., or the Motorola m500 or m25 Digital Audio Players, manufactured by Motorola Inc. of Schaumburg, Ill. In still other embodiments, the computing device 100 is a portable media player, such as the Zen Vision W, the Zen Vision series, the Zen Portable Media Center devices, or the Digital MP3 line of MP3 players, manufactured by Creative Technologies Ltd. In yet other embodiments, the computing device 100 is a portable media player or digital audio player supporting file formats including, but not limited to, MP3, WAV, M4A/AAC, WMA Protected AAC, RIFF, Audible audiobook, Apple Lossless audio file formats and .mov, .m4v, and .mp4 MPEG-4 (H.264/MPEG-4 AVC) video file formats.

In some embodiments, the communications device 102 includes a combination of devices, such as a mobile phone combined with a digital audio player or portable media player. In one of these embodiments, the communications device 102 is a smartphone, for example, an iPhone manufactured by Apple Computer, or a Blackberry device, manufactured by Research In Motion Limited. In yet another embodiment, the communications device 102 is a laptop or desktop computer equipped with a web browser and a microphone and speaker system, such as a telephony headset. In these embodiments, the communications devices 102 are web-enabled and can receive and initiate phone calls. In other embodiments, the communications device 102 is a Motorola RAZR or Motorola ROKR line of combination digital audio players and mobile phones.

In some embodiments, the status of one or more machines 102, 106 in the network 104 is monitored, generally as part of network management. In one of these embodiments, the status of a machine may include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information may be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

B. Network Analyzer

Systems and methods of the present solution are directed to a network analyzer that helps clients and prospective clients evaluate and optimize their use of the network. In one implementation, the network may be a health care provider network, and the network analyzer may help clients and prospective clients evaluate and optimize their use of PPO networks, which are a type of health care provider network. Through this evaluation and optimization process, clients and prospective clients can make better decisions regarding their PPO network that will lower costs, increase profits, and maximize their net savings. Although embodiments of the present solution may be discussed below in the context of PPO networks, the present solution is applicable to any type of health care provider network.

One embodiment of the network analyzer is an interactive analysis tool that allows a user to observe the impact of different network configurations based on actual experience measured against a comprehensive bill review database. The tool analyzes the actual bill review database in order to create a model profile. The model profile represents an emulation of billing-related decisions, such as discounts, made by a PPO network. By comparing the model to actual results for the same configuration, a baseline is established for comparison to other networks. The results being compared may include total charges, bill review allowance, amount billed to the PPO, PPO reduction, PPO discount, penetration, and PPO efficiency. The user may change the configuration to a different set of PPO networks. The tool will then emulate billing decisions for the new configuration of networks and provide updated results. The user may repeat this process to optimize the results, or the tool may automatically analyze all network configurations for an optimal result.

The tool provides a plurality of ways for a user to view, analyze, understand, and validate the results. The results may be accessed and tracked interactively and/or through summary reports. The results may be broken down by any category. For example, the results report may be viewed as a breakdown by PPO and type of service for each network showing detailed penetration and savings down to the individual tax identification number level. In another embodiment, the results report may show a comparison by type of service and tax identification number of actual penetration and savings versus the model. In yet another embodiment, the results report may be a summary showing the level of detail actually used by the model for each match in determining the estimated savings. The report may, in another embodiment, show a summary of the distinct tax identification numbers for each network in the jurisdiction. The user may, via the interactive user interface, create customized reports using one or more categories.

The systems and methods of the network analyzer provide a plurality of benefits. For example, the network analyzer allows a user to evaluate multiple networks and stacking orders quickly and easily. In another embodiment, the user can objectively evaluate each network using the same criteria, thus eliminating the biases and inconsistencies when networks do their own analysis. Increased accuracy is another benefit provided by calculating savings at the service level for each provider for each network for each jurisdiction, rather than just using network averages. Using the systems and methods of the network analyzer results in savings calculations that are more accurate, and also allows the user to drill down into the data and analyze exactly what factors are providing these savings.

Figure 2A:
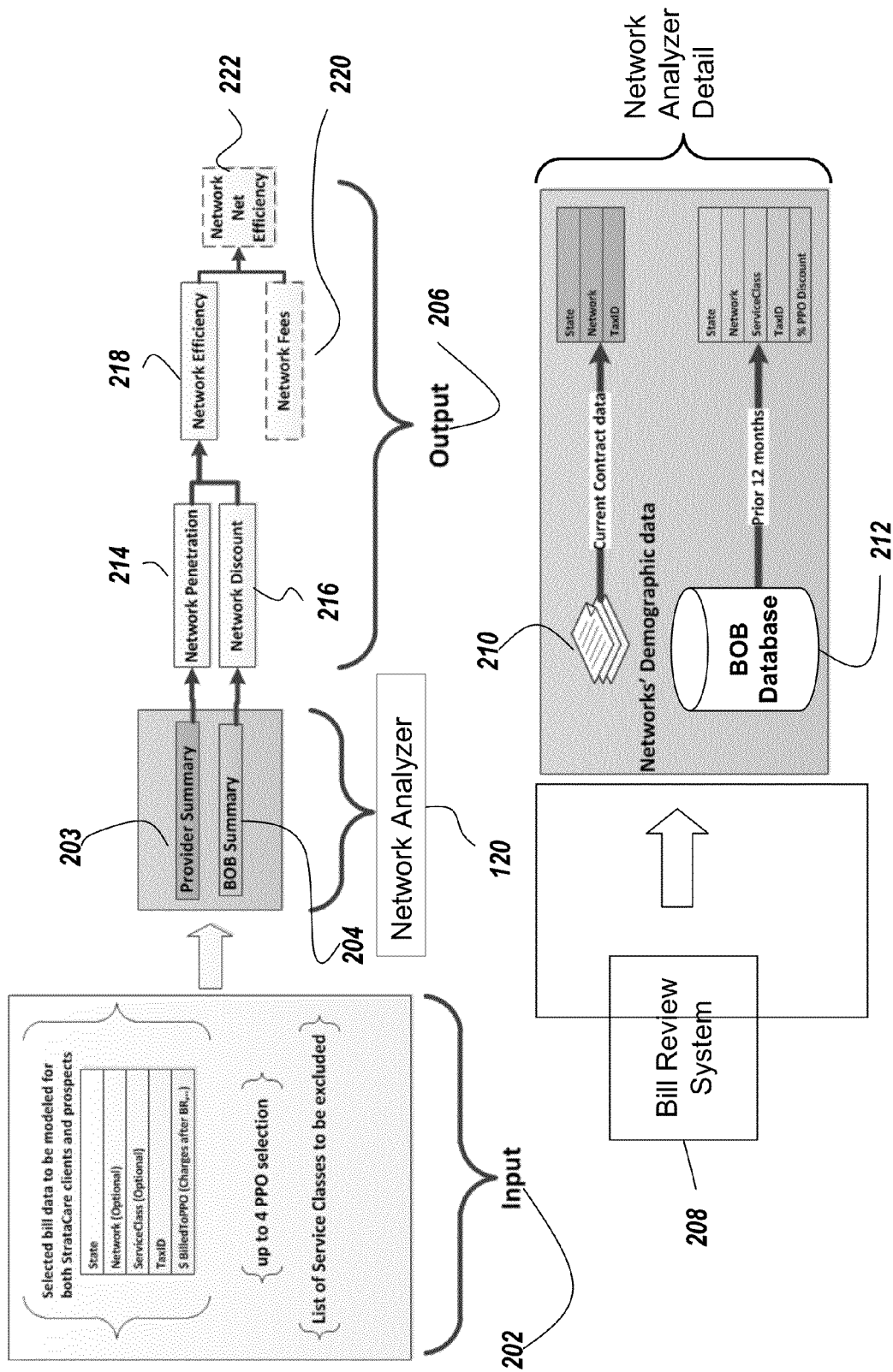
FIG. 2A is an embodiment of a system comprising a network analyzer.

Referring to FIG. 2A, an embodiment of a network analyzer system is depicted. In brief overview, the system receives user input and obtains data from a plurality of modules, including, e.g., an input module 202, bill review system 208, demographics module 210, and book of business ("BOB") database 212. Using this user input and data, the network analyzer module generates a provider summary, via provider summary element 203, and a BOB summary, via BOB summary element 204. These summaries organize the plurality of data and input received by the tool. Using these summaries, the tool determines a network penetration, via network penetration element 214, a network discount, via network discount element 216, a network efficiency, via network efficiency element 218, network fees, via network fees element 220, and a network net efficiency, via network net efficiency element 222. The output module 206 may display some or all of the input or calculations performed by the system in a plurality of formats, including, e.g., a spreadsheet or report via a graphical user interface.

The bill review system 208 may comprise an application, program, library, script, service, process, task or any type and form of executable instructions executing on a client 102 or a server 106. The bill review system may interface with a plurality of modules via network 104 or in any other way. Bill review may refer to the process of reviewing health care or worker's compensation or disability related bills for health care services to determine whether some or all of the bill should be paid for by the insurance company and/or the insured, and what their respective contributions should be. Bill review may also refer to the process of reviewing reimbursement requests from the insured and making a similar determination. For example, the bill review system may be a system or service such as any of the products and services provided by Stratacare, LLC of Irvine, Calif. The bill review system may be configured to interface with medical providers, insurance companies, electronic bill payment vendors, etc. The data provided by the bill review system may include any and all information related to medical bills, medical bills allowed by bill review, medical services, patients, health care providers, tax identification numbers of health care providers, PPOs, states, etc. The bill review system may provide historical data, data in real-time, or projected data. The data provided as input to the network analyzer may be filtered for a specific time range, class of services, geographical location, PPO, or in any other way.

In further detail, the network analyzer system may include an input module 202 designed and constructed to interface to any type and form of input source. The input module may comprise an application, program, library, script, service, process, task or any type and form of executable instructions executing on a client 102 or a server 106. The input module may interface with input sources via network 104, a user interface, etc. In one embodiment, the input module 202 may be configured to interface with a bill review system 208. In this embodiment, the input module provides bill review data to the network analyzer 120.

In some embodiments, the input module 202 may employ a user interface. The user interface may be any type or form of interface, such as a graphical user interface (GUI) and/or a command line interface. The interface may be a web interface. The interface may be an application interface. The interface may be an application executing on a mobile device, such as what is commonly referred to as an "app" executing on a smart phone. Portions of the interface and interface content may be provided by a locally-executing application (e.g., software program) on a client machine 102. Portions of the interface and interface content may be remotely transmitted from a server 106 to a client machine 102 for presentation (e.g., on a browser executing on the client machine 102).

The user interface may present and provide access to the functionality, operations and services of the network analyzer. To implement the functionality of the network analyzer, the interface may include any number of user interface components generally referred to as widgets. A widget may comprise any one or more elements of a user interface which may be actionable or changeable by the user and/or which may convey information or content. For example, a widget may be an input text box, dropdown menu, button, file selection, etc. Interface widgets may comprise any type and form of executable instructions that may be executable in one or more environments. Each widget may be designed and constructed to execute or operate in association with an application and/or within a web-page displayed by a browser. One or more widgets may operate together to form any element of the interface, such as a dashboard. The user interface may include any embodiments of the user interfaces described in FIGS. 3A-3G or any portions thereof or functionality provided by such user interfaces.

The input module 202 may require certain user input for the network analyzer to evaluate efficiency, while other input may be optional. In some embodiments, the input includes state, health care provider tax identification number, and amount billed to the PPO. The input may also include a selection of a plurality of PPOs and a selection of a plurality of service classes to be excluded from evaluation. A service class may be any type of service class, including, e.g., radiology, drugs, surgery, medicine, durable medical equipment, facility-outpatient hospital, medical and surgical supplies, anesthesiology, evaluation and management, physical medicine and rehab, medical legal, pathology, transportation, orthotic procedures and devices, non-medical, etc. The number of PPOs that can be selected may vary, be limited to a predetermined maximum number, or be automatically selected by the tool based on a plurality of factors. For example, the network analyzer may automatically determine that there are only three PPO networks that satisfy the state and service class selected by the user. In this example, the user may select one or more of these PPO networks for evaluation. The network analyzer may also receive input regarding service classes to be excluded for analysis.

The network analyzer module 120 may be designed and constructed to receive a plurality of inputs, perform a plurality of functions, and display a plurality of outputs. The network analyzer 120 may use a plurality of elements to perform these functions. In one embodiment, the network analyzer 120 comprises a provider summary element 203, networks' demographic database 210, a book of business database 212, a network penetration element 214, a network discount element 216, a network efficiency element 218, a network fees element 220, and a network efficiency element 222. The network analyzer module 120 and associated elements and databases may comprise an application, program, library, script, service, process, task or any other type and form of executable instructions executing on one or more clients 102 and/or servers 106.

The networks' demographic database 210 may contain demographic data corresponding to health care providers, PPO networks, and/or the insured. The database may be updated in real-time, or at any other period. The demographic data is received via the bill review system 208, a PPO database, health care provider, or from any other data source via network 104. Demographic data may include any data about the health care provider, PPO network, and/or the insured that may be used by the tool to evaluate a network. For example, networks' demographic data may be information about the health care provider that includes, e.g., the state the health care provider practices in, the PPO network(s) they are associated with, their tax identification number, address, name of the practice, etc.

The provider summary 203 is the system calculated output from the 202 input. The provider summary may be in any form or format, such as a file, data structure, or object. The system may create the provider summary on a periodic basis or in real-time. In one embodiment, the provider summary is created on a monthly basis. The system may use data from any data source. In one embodiment, the system uses data from the networks' demographic database 210. In another embodiment, the system may use data from the input module 202 and/or the BOB database 212. The provider summary contains information about the health care service provider, including, e.g., the state the provider practices in, the PPO network(s) the provider is associated with, the tax identification number of the provider, and the type of record. The type of record field may be either a core record from the BOB database or a client PPO record.

The book of business ("BOB") database 212 contains a plurality of data that may be used by the network analyzer to evaluate the efficiency of a network. The data may be stored in any format and organized in any way. Each data entry may contain one or more fields that facilitate data processing. The BOB database may contain the type of data provided by the bill review system 208 for a plurality of entities. For example, the BOB database may contain any information about each health care bill, including, e.g., state, PPO network, tax identification number of the health care provider, service class, count, whether the bill was allowed by bill review, whether the bill was allowed by the PPO, discount, etc. The BOB database may be organized by entity, insured, insurance company or in any other way. The BOB database may contain historic data for a plurality of years. The BOB database may be updated on a periodic basis or in real-time via network 104 or in any other way. The BOB database 212 may be stored on a client 102 or server 106. The BOB database may be accessed by the network analyzer module via network 104, or any other way.

The BOB summary element 204 is designed and constructed to create a BOB summary (also referred to as "PPO summary") in any form or format, such as a file, data structure or object. The element may create the BOB summary on a periodic basis or in real-time. In one embodiment, the BOB summary is created on a monthly basis. The element may use data from any data source. In one embodiment, the element uses data from the BOB database 212. In another embodiment, the element may use data from the input module 202 and/or the networks' demographic database 210. The element may be configured to filter out data on a plurality of factors. For example, the element may be configured to create a BOB summary that only contains data for a certain time range, service class, bills falling within an amount range, etc. In some embodiments, the element may account for situations where there is missing data. For example, the tool may have access to all necessary information if the user is a client. However, the tool may not have access to all bill review data if the user is a prospective client who has not provided the tool with access to all bill review data. If, for example, the tool does not have access to discount values of every service class for a provider, the BOB summary element may account for the missing data in a plurality of ways. In one embodiment, the element may use the average discount for the provider for all bills to estimate a discount for a service class. In another embodiment, the element may use the average discount for that service class in the PPO network to estimate the discount of a service class for a particular provider.

In one embodiment, the BOB summary element 204 is designed and constructed to create a BOB summary that contains state, network, tax identification number, service class, bill count, amount allowed by bill review, amount allowed by the PPO, and the discount. Some or all values may be determined using data from the BOB Database 212, networks' demographic database 210. In one embodiment, the element may retrieve the state, network, tax identification and service class information from the. The element may determine, using retrieved data, the bill count, amount allowed by bill review, amount allowed by the PPO, and the discount.

The network analyzer tool may comprise an application, program, library, script, service, process, task or any other type and form of executable instructions executing on a client 102 or a server 106. The network analyzer tool may comprise a network penetration element 214 that is configured to use a plurality of input data and/or data stored in the database to determine a network penetration value and output that determination in one or more forms. The network penetration element may output the final determination or any intermediate steps. The network penetration element may output the determined value to another element, a computer readable memory, a user interface, a client 102, and/or server 106. In some embodiments, the output may be transmitted via a network 104. The determinations may be performed in real-time, a batch job, or at any other interval. The determination may be made using data from a plurality of data sources. In one embodiment, network penetration may represent the percentage of bills being charged to one PPO as compared to a plurality of PPOs. For example, the element may determine network penetration for a client, using input data and/or data from the bill review system, as a total of bill reviewed charges allowed for a selected health care provider network divided by a total of bill reviewed charges allowed for a plurality of health care provider networks. The determination may be made for any subset of categories or combination of categories, including, e.g., on a per service class basis for a selected health care provider network, a time period, for services performed within a state, etc.

The network analyzer may comprise a network discount element 216 that is configured to use a plurality of input data and/or data stored in the database to determine a network discount value and output that determination in a plurality of forms. The network discount represents the reduction in price for a health care service as a result of the health care provider being associated with the PPO network. In some embodiments, the network discount may be received via a plurality of data sources. In another embodiment, the network discount may be determined using data from a plurality of data sources. The network discount element may output the final determination or any intermediate steps. The network discount element may output the network discount value to another element, a computer readable memory, a user interface, a client 102, and/or server 106. In some embodiments, the output may be transmitted via a network 104. The determination may be performed in real-time, a batch job, or at any other interval. In one embodiment, the element may determine network discount using data from the bill review system. The determination may be made for any subset of categories or combination of categories, including, e.g., on a per service class basis for a selected health care provider network, a time period, for services performed within a state, etc.

In some embodiments, the network analyzer module may be designed and constructed to determine a savings for an individual client using the PPO summary. To determine a savings, the network analyzer module may first determine a discount value and then multiply the discount value by the amount allowed by bill review. Since client bill data may not contain a discount value, the module may determine discount value using other information. In one embodiment, the network analyzer module matches a client bill to a corresponding record in the PPO summary and retrieves the discount value stored in the PPO summary. For example, the network analyzer module may generate a client summary table using client account data. The user may select data parameters, including, e.g., the account, time range, whether to exclude converted bills, and whether to exclude a service class. The network analyzer module then summarizes the bills in the client summary table by record identification, state, network, tax identification number, and service class. Thereafter, the network analyzer module may match the records in the client summary table with records in the provider summary table. The records are matched based on state and tax identification number. For each match, the corresponding record in the PPO summary table is found based on state, network, service class, and tax identification number. If a full match is made, then the corresponding discount value is retrieved and stored, accordingly, in the client summary table. If a complete match is not found, the network analyzer module may search for a partial match based on state, network, and service class. If this match is found, the corresponding discount value is retrieved and stored, accordingly, in the client summary table. If this partial match is not found, the module may perform another search based on state and network. If this match is found, the corresponding discount value is retrieved and stored. If there is a plurality of discount values for this match, the average discount value may be stored. The discount value stored in the client summary table may be used for all further determinations and calculations based on a specific client.

The network analyzer may comprise a network efficiency element 218 that is configured to use a plurality of input data and/or data stored in the database to determine a network efficiency value and output that determination in a plurality of forms. The network efficiency may represent the quality of one or more PPO networks and may be determined by, e.g., using the network discount value and network penetration value. In some embodiments, the network efficiency value may be received via a plurality of data sources. In another embodiment, the network efficiency may be determined using data from a plurality of data sources. The element may output the final determination or any intermediate steps. The element may output the network efficiency value to another element, a computer readable memory, a user interface, a client 102, and/or server 106. In some embodiments, the output may be transmitted via a network 104. The determinations may be performed in real-time, a batch job, or at any other time. In one embodiment, the element may determine network efficiency using data from the bill review system. The determination may be made for any subset of categories or combination of categories, including, e.g., on a per service class basis for a selected health care provider network, a time period, for services performed within a state, etc.

In one embodiment, the network analyzer may comprise a network fees element 220 that is configured to use a plurality of input data and/or data stored in the database to determine the fees related to a PPO network. The fees may be related to transaction costs, overhead, administrative fees, or any other fees related to a PPO network. Fee information may be received directly from the PPO network via network 104, stored in a database, input via the input element 202, input via the bill review system 208, etc. The network fees may be determined in real-time, a batch job, or at any other time. The network fees may be determined for any subset of categories or combination of categories, including, e.g., on a per service class basis for a selected health care provider network, a time period, for services performed within a state, etc.

In some embodiments, the network analyzer may comprise a network net efficiency element 222 that is configured to use output from one or more elements, input data, and/or data stored in the database to determine a network net efficiency value and output that value in one or more of a plurality of forms. The network net efficiency may represent the quality of one or more PPO networks after all deductions have been taken into account. The element may determine the network net efficiency by, e.g., accounting for network fees when determining network efficiency. In some embodiments, the network net efficiency value may be received via a plurality of data sources. In another embodiment, the network net efficiency may be determined using data from a plurality of data sources. The element may output the final determination or any intermediate steps. The element may output the network net efficiency value to another element, a computer readable memory, a user interface, a client 102, and/or server 106. In some embodiments, the output may be transmitted via a network 104. The determinations may be performed in real-time, a batch job, or at any other time. In one embodiment, the element may determine network net efficiency using data from the bill review system. The determination may be made for any subset of categories or combination of categories, including, e.g., on a per service class basis for a selected health care provider network, a time period, for services performed within a state, etc.

The output module 206 is designed and constructed to provide the results of the network analyzer to a user in a plurality of ways. In one embodiment, the output module may comprise a user interface. The output module may be configured for interactive analysis, or to provide a report. The report parameters and format may be predetermined, or determined by the user via the user interface. The report parameters may include, e.g., state, excluded service classes, primary network, and a plurality of secondary networks. In some embodiments, the report may be a spreadsheet. In another embodiment, the report may be a table on a graphical user interface. The output module may be configured to provide additional information regarding each entry in the report. For example, a user may select on an entry, via a mouse, keyboard or any other input/output device. Upon selection, the output module may provide additional information about the entry. For example, one embodiment of the results report may group all bills by service classes, where each row in a table represent a service class. The column corresponding to tax identification number of the health care provider that performed the service may be blank because a plurality of health care providers may have provided services that are grouped within the given service class. In this example, the user may select the blank entry corresponding to a service class row and a tax identification column. Upon selection, the output module may provide tax identification numbers corresponding to each health care provider that provided a service grouped within that service class. One with ordinary skill in the art can appreciate the plurality of ways to provide additional data about each entry in the results report.

Figure 2B:
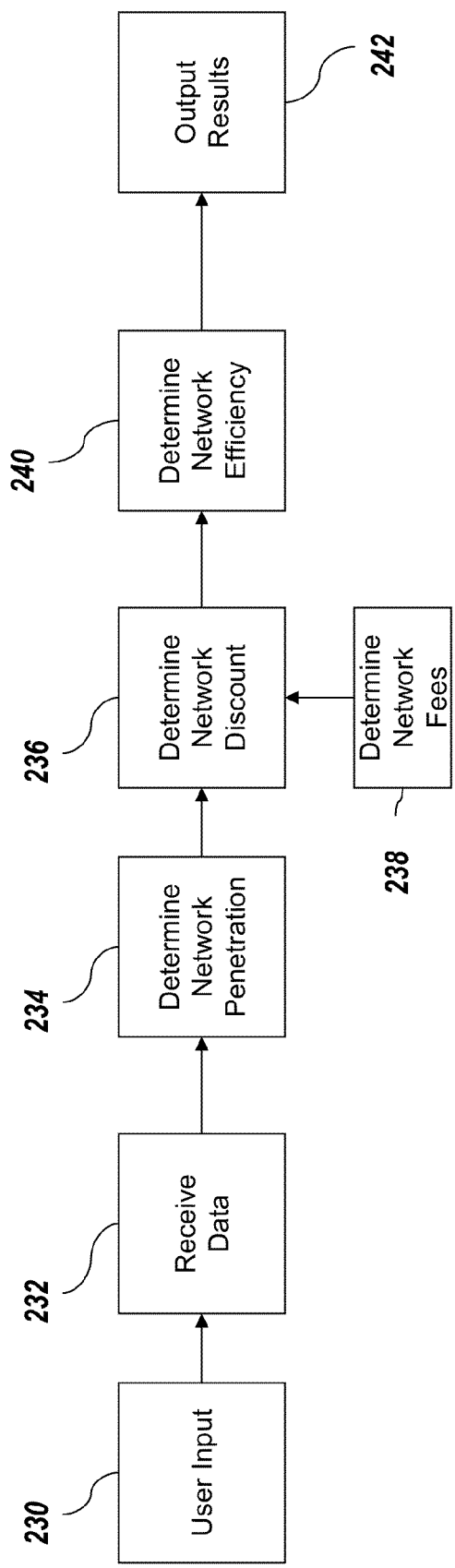
FIG. 2B is a flow diagram depicting an embodiment of a method of using the network analyzer.

Referring now to FIG. 2B, embodiments of a method for network optimization is depicted, including, e.g., a method for evaluating efficiency of billing services via a health care provider network. In brief overview, a user may input data and/or make a plurality of selections at step 230. The selections may relate to PPO networks or direct the tool to make certain determinations or output data in a certain form. At step 232, the network analyzer receives a plurality of data. The data may be from the bill review system or any other data source. At step 234, the network analyzer determines a network penetration value using the user input and received data. At step 236, the network analyzer determines network discounts using received data and/or user input. In one embodiment, the network analyzer may account for network fees at step 238. At step 240, the network analyzer determines a network efficiency using generated or received data, calculations, and other values. At step 242, the network analyzer may output the results and any intermediate steps in a plurality of forms.

In further detail, at step 230, the network analyzer receives a plurality of user input. In some embodiments, the user input is received via the input module 202. The input may include any data relating to the user, client, insured, insurance entity, and/or PPO network. For example, the user may input a state, network, service class, health care provider tax identification number, client identification, customer identification, and/or the amount charges after bill review. In one embodiment, the input may include selections made by a user. For example, the user may select one or more PPO networks to be evaluated by the network optimization tool, one or more states, service classes to include or exclude, time periods for evaluation, etc. In some embodiments, the user may select up to four health care provider networks. In another embodiment, the user may select any or all available health care providers. In various embodiments, the network analyzer can be configured to receive a range of health care provider networks for evaluation. In one embodiment, the list of selections may be automatically populated based on a plurality of factors. For example, based on the one or more states selected by a user, the list of PPO networks that may be selected may comprise of only PPO networks operating in the previously selected state(s). In another embodiment, the user may select a health care provider network or PPO, and the network analyzer may automatically filter the number of states presented for user selection based on the states in which the health care provider network provides services. In some embodiments, the network analyzer may account for the time period entered for evaluation, service class, etc. In another embodiment, the service class type may determine which PPO networks may be selected by the user. In another embodiment, they user may select the form of output. For example, the user may prefer the output to be in the form of a spreadsheet, graph, list, etc. In some embodiments, the user may select that the output be displayed via a GUI and/or have a physical copy sent.

In some embodiments, the user selects via the user interface of the network analyzer a selection of one or more healthcare provider networks, such as a PPO. The user may also select via the user interface of the network analyzer a state for which services were provided by the selected healthcare provider network. The user may select from any of the options from the fields or user interface elements provided by the example embodiment of the user interface of the network analyzer illustrated in FIG. 3A, such as a report type, account level, client, customer, from and to date range, excluded services classes and primary network. In some embodiments, the user identifies via the user interface of the network analyzer a time period for determining the penetration efficiency and/or savings.

At step 232, the network analyzer may receive, query or obtain a plurality of data for performing an analysis responsive to the user's selections. In some embodiments, the data may be received via the input module 202. The data may be received from a plurality of data sources. The data may be anything related to the user, client, insured, insurance entity, and/or PPO network that can be used by the tool to evaluate a network. In one embodiment, the data source may be the bill review system 208. The bill review system 208 may contain a plurality of data, including, e.g., information about health care bills, services, total charges, charges allowed by bill review, charges billed to a network, location, networks, network discounts, and/or network fees. In some embodiments, step 232 may include filtering the received data based on a plurality of factors. Factors may include, for example, PPO network, service class, state, health care provider tax identification number, etc. In one embodiment, the filtering criteria may be selected via the user input at step 230. For example, if a user, at step 230, excludes a particular service class from the network evaluation, the tool may filter out some or all data associated with the excluded service class.

At step 234, the network analyzer determines a network penetration. In one embodiment, the network penetration element 214 may determine the network penetration. In one embodiment, network penetration may represent the percentage of bills being charged to one health care provider network or PPO as compared to a plurality of health care provider networks or PPOs. For example, the element may determine network penetration for a client, using input data and/or data from the bill review system, as a total of bill reviewed charges allowed for a selected health care provider network divided by a total of bill reviewed charges allowed for a plurality of health care provider networks. One or more selections made by the user at step 230 may be used to determine the network penetration. For example, the network penetration may be determined for a selected time period, service type, state, geographic location, and/or entity, etc. In one embodiment, the network analyzer can, at step 234, determine a penetration and a savings for bills on services within the state for the selected health care provider network. In another embodiment, the network analyzer can determine the penetration efficiency and the savings for bills on services within the state for the selected health care provider network during the time period the user input at step 230. In another embodiment, the network analyzer can determine the penetration efficiency and the savings for bills on service within the state for a plurality of health care provider networks. For example, the user may, at step 230, input four health care provider networks and the network analyzer may determine penetration efficiency, savings, and a plurality of other values for one or more of these health care provider networks.

At step 236, the network analyzer can determine a network discount. In one embodiment, the network discount element 216 may determine the network discount. The network discount represents the reduction in price for a service as a result of the service being performed by a health care provider associated with the PPO network. The network discount may be determined in a plurality of ways and be based on a plurality factors, including, e.g., state, service class, time period, health care provider, etc. In one embodiment, the bill review data may be used to determine the discount. For example, the discount may be the difference between the full price of a service and the reduced in-network price. In another embodiment, the discount may be determined using a percentage discount of a network. For example, the tool may receive input, via steps 230 or 232, about a discount for a class of services performed by a service provider in the network. The discount may vary based on the service class and/or service provider. In some embodiments, the network discount can be used to determine the savings for a network. The savings may be based on a discount of the selected health care provider network applied to a total amount saved from bill review of charges for the selected health care provider network.

In some embodiments, the network analyzer can determine savings based on a plurality of selections. In one embodiment, the network analyzer can determine penetration and/or savings on a per service class basis for the one or more health care provider networks. In another embodiment, the network analyzer can determine the penetration and savings excluding one or more service classes. For example, the network analyzer may determine penetration and savings for all service classes that are part of a health care provider network except for drugs.

At step 238, the network analyzer can determine a fee charged by the network. In one embodiment, the network fees element 220 may determine the network fee. The network fee may include overhead, administrative fees, transaction costs, or any other fees related to a PPO network. A network fee may be associated with a particular state, service class, client, or any other category. In another embodiment, the network fee can be based on a percentage of savings, which may vary by State and/or a per bill basis. In one embodiment, the network analyzer may account for network fees when determining the total network discount. For example, a network fee may be associated with a service class. When determining the total discount received for that service class, the network analyzer may account for the network fees. By accounting for network fees, a net network efficiency can be determined at step 240.

At step 240, the network analyzer can determine a network efficiency. In one embodiment, the network efficiency element 218 can determine the network efficiency. The network efficiency represents the quality of one or more PPO networks and may be determined by, e.g., using the network discount value and network penetration value. A plurality of data generated or received at various other steps can be used to determine the network efficiency. In one embodiment, the element may determine network efficiency using data from the bill review system. The determination may be made for any subset of categories or combination of categories, including, e.g., on a per service class basis for a selected health care provider network, a time period, for services performed within a state, etc. In one embodiment, the network efficiency is determined by multiplying PPO network discount and network penetration.

In some embodiments, the network analyzer can compare the penetration, savings, discount, and/or network efficiency of one health care provider network to another. For example, the use may select a plurality of health care provider networks. The network analyzer can determine a plurality of metrics, including, e.g., penetration, savings, discount, and/or network efficiency, for each health care provider network and determine a percentage difference from one health care provider network to another. In another embodiment, the network analyzer may provide a comparison of efficiency of billing of services for a plurality of clients. For example, the user may select a client from a plurality of clients via the user interface. The network analyzer may compare the efficiency of billing of services for the selected client between a plurality of selected health care provider networks. In another embodiment, the network analyzer may rank the plurality of health care provider networks based on one or more of these metrics.

At step 242, the network analyzer outputs the results of the network evaluation and optimization. The network analyzer may output the results in a plurality of ways. In one embodiment, output module 206 can output the results. The results may be outputted in any format and be based on any set of parameters. The format may be predetermined, selected by the user, or automatically determined in real-time by the system. The results may be output in a spreadsheet, graph, and/or table via a user interface. The report may be static or interactive. The report may be based on a plurality of parameters, including, e.g., state, excluded service classes, primary network, and a plurality of secondary networks. The report may display a plurality of data and results, including, e.g., PPO name, total charges, charges allowed by bill review, charges billed to the PPO, PPO reduction (or savings), PPO discount (%), penetration (%), and PPO efficiency (or effectiveness).

In another embodiment, the systems and methods described may be used to automatically determine an optimal network configuration. For example, the network analyzer may evaluate every combination of networks available in a state to determine which combination would provide the maximum reduction in costs and maximum PPO efficiency. In this embodiment, a user may not have to select individual networks for evaluation. In one embodiment, a user may select a subset of PPO networks for the network analyzer to use in automatically determining the optimal network configuration.

Referring now to FIG. 2C, embodiments of data retrieved and calculations performed by the systems and methods described above are shown. This spreadsheet may also be an embodiment of an output results report. In brief overview, a plurality of rows represent a PPO network, and a group of rows 252-260 represent a configuration of PPO networks. Each configuration of networks contains a "total" row that is a summation of values associated with a column. Each column represents a category of data corresponding to a PPO network, including, e.g., PPO name, total charges, BR allowance, billed to PPO, PPO reduction, PPO discount, Pen($) and PPO Eff.

In further detail, network configuration group 252 represents data and calculations using actual data from the bill review system. In this example, there are five network configurations: Interplan, No PPO, Beech Street Termed, USC Pend and Transmit, and Beech Street PPO. No PPO refers to the lack of a PPO network and is treated similar to a PPO category for the sake of illustration. The total charges column represents the total charges for services performed by health care providers associated with the network. The BR allowance column represents the charges allowed after bill review. The billed to PPO column represents the charges that were billed to the PPO networks. The PPO reduction column represents the savings provided by the PPO network. The PPO discount column represents the percent discount provided by the PPO network. This discount percentage is determined as the PPO reduction for a network divided by the total billed to the PPO network, multiplied by 100. For example, the Actual 252 Interplan PPO discount is ((260,019)/(3,569,695))

*100=7.28%. The penetration column represents the amount that is billed to a PPO network as compared to the remaining PPO networks in the network configuration. The penetration percentage is determined as the amount billed to PPO divided by the total billed to all PPOs in the network configuration. For example, the Actual 252 Interplan penetration is ((3,569, 695)/(7,020,770)*100)=50.84%. The PPO efficiency is determined as the penetration percentage multiplied by the PPO discount percentage, divided by 10. For example, the Actual 252 Interplan PPO efficiency is (7.28*50.84)/10=37.04. These calculations may be performed for each PPO network in each PPO network configuration 252-260.

Category 254 represents a model of the actual PPO configuration. Modeling the actual PPO configuration is the same as modeling any other PPO configuration. The tool may use anywhere from two to ten or more PPOs to create the model configuration. In some embodiments, the tool may use four PPOs for the model. The purpose of the model is to make sure or verify the result of the model of actual and the actual configuration are relatively close. This established a confidence level for the exercise. The model of actual may serve as a benchmark when modeling other PPO configurations. Any bias introduced by the model may be eliminated by using the model of the client's configuration as the basis of comparison to other theoretical configurations.

When fewer PPOs are selected for the model as compared to the actual, the tool intelligently allocated bills to the available PPO. In the example illustrated in FIG. 2C, the actual PPO configuration consists of Interplan, No PPO, Beach Street Termed, USC Pend and Transmit, and Beech Street PPO. The model of actual consists of all these PPOs except for Beech Street Termed. Thus, the tool may allocate the bills charged to the Beech Street Termed PPO in the actual configuration among the four PPOs selected for the model configuration in a plurality of ways. In one embodiment, the tool may determine which of the four available PPOs provides the highest discount for that bill based on a plurality factors, including, e.g., service type, geography, provider, etc. In another example, the tool may allocate those bills to No PPO. In yet another embodiment, the tool may allocate those bills based on which PPOs have not exceeded a billing limit.

In the example illustrated in FIG. 2C, the model of the actual PPO configuration for the client is shown in category 254. The tool selected four PPOs used by the client for the model: Interplan, Beech, USC, and No PPO. The results are close: the model of actual has a 49.36 PPO efficiency, and the actual efficiency is 42.48. When alternate models are run, the efficiency is compared to the 49.36 efficiency of the model.

The total row for each network configuration 252-260 represents the total determined for each column category. The total entry for Total Charges, BR allowance, Billed to PPO and PPO reductions are determined by summing their respective rows. For example, the total entry for Total Charges is a sum of the Total Charges for Interplan, No PPO, Beech Street Termed, USC Pend And Transmit, and Beech Street PPO. The calculations is as follows: 10657974+8086362+476990+235577+334548=19791451. The total entry for PPO Discount is determined as the total PPO Reduction divided by the total billed to PPO networks, not including the amount billed to No PPO. For example, ((total PPO Reduction)/(total billed to PPO−amount billed to No PPO))*100=((298,231)/(7,020,770−3,049,978)) *100=7.51%. The total penetration, similarly, is a sum of all the penetration values minus the penetration value for No PPO. The total PPO efficiency represents how efficient the PPO network configuration is. The total penetration efficiency is determined as a sum of all the PPO efficiencies. One goal of the network analyzer is to maximize the total PPO efficiency number by comparing various configurations of networks. For example, the configuration of PPO networks in Profiler-Result 256 has the highest PPO efficiency value, thus making the ProfilerResult configuration the optimal configuration of PPO networks for this set of bill review data. Using these results, a client or user of the network analyzer may decide to use the PPOs shown in ProfilerResult 256.

Referring to FIG. 3A, an illustration of a graphical user interface of the network analyzer is shown. This interface may employ any of the systems and methods described above. In brief overview, a user enters input via the user interface, the tool analyzes the input and other data, and then the results are displayed via a graphical user interface. The user input may comprise any of the input discussed in connection with the input module 202, the user step 230, and/or the receive data step 232.

In further detail, the user may select a report type from the "Report Type" drop down menu. The report type determines input for the report, e.g., whether the tool uses existing data or prospective data for the analysis. The user may then enter their identification information in the "Customer" input box. The customer may refer to a client of the entity providing a bill review service, bill review data, and/or the network analyzer. If the customer information is previously saved, the user may select the saved customer information from a drop down menu. The user may perform the analysis for a specific client by selecting an account level and a client. The account level may refer to the level or amount of data to provide to the network analyzer for the purpose of analysis. The account level may also refer to specific sources of the data. The levels may refer to a user's clients, offices, region, etc. Every user may have a different account hierarchy, so the levels may be customized to represent various levels to various clients. The tool can model the bills at any level of the customer hierarchy. The user may select "all" account data or the user may select a subset of account data. The data source may be any source accessible to the network analyzer via a network 104, or by any other means. A user may have a plurality of clients, so the user may select one or more clients for the analysis via the "Client" drop down menu. The user may then select the state from the "State" dropdown menu. The user may then select a time range for the analysis. For example, the user may select a "From" date and a "To" date. The time range may be limited to the amount of data that is available for the client. The user may then exclude one or more service classes via the "Exclude Service Class" drop down menu. The user may then select a primary network for analysis from the drop down menu. This drop down menu may be automatically populated with PPO networks available in the selected state. In this example, the primary network is First Health Pend and Transmit. The user may choose three additional networks to analyze.

In this illustration, the results of the analysis are displayed below the input section of the graphical user interface. The report display includes a title along with additional information about the analysis setup. The results are displayed in a table similar to the table described in conjunction with FIG. 2C. Following the results, a user may select to view addition detail about the analysis and data. In this illustration, the user may select "Model Detail," "Actual Detail," or "Other." These fields will be discussed further below.

Figure 3B:
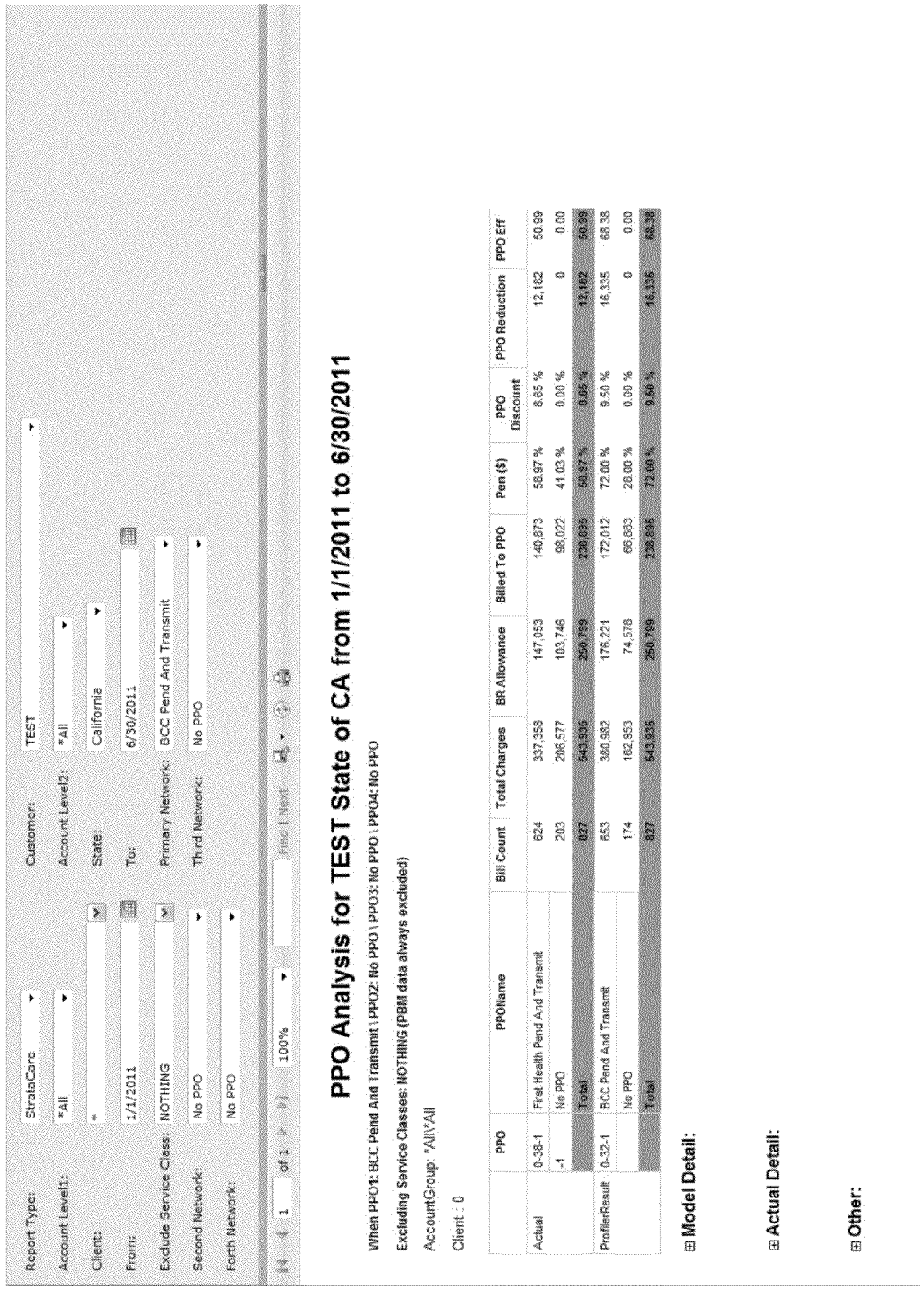

Referring now to FIG. 3B, an illustration of a graphical user interface of the network analyzer is shown. This display is similar to that of FIG. 3A and shows the ability of the user to select a different Primary Network for comparison purposes. In this example, the Actual data used for the analysis is based on the First Health Pend and Transmit PPO network. However, the user has chosen to compare the performance of this network with another network, the BCC Pend and Transmit PPO network. As shown in the report, the results for the second network are superior to that of the first network. For example, the PPO efficiency is 68.38, which is an increase from 50.99. Thus, the user, by comparing these two networks, can determine which is the optimal PPO network.

Referring now to FIG. 3C, an illustration of additional detail in a network analyzer results report is shown. The report is similar to those discussed above. In addition to the results table, the user may select additional fields in order to better analyze, understand, and evaluate the results from the network analyzer. For example, the user may expand the Model Detail field by selecting the "+" button to the left of "Model Detail." The user may select the type of detail to view. In this example, the user may analyze the results By PPO/Service Class/TaxID. This is a breakdown by PPO and type of service for each network showing detailed penetration and savings down to the individual tax identification level. The user may analyze the results By PPO/TaxID. This is a breakdown by PPO network showing detailed penetration and savings down to the tax identification number. The user may analyze the results By Service Class\PPO\TaxID. This is a breakdown by type of service and PPO for each network showing detailed penetration and savings down to the individual tax identification level. Similarly, the user may request to view additional detail for the Actual data.

The user may view additional detail under the "Other" category. The user may choose to view the results based on Pricing Hierarchy Match. The pricing hierarchy match is a summary showing the level of detail actually used by the model for each match in determining the estimated savings. The user may view the PPO TaxID count in state. This view is a summary of the distinct tax identification numbers for each network in the jurisdiction. The user may view the Model vs. Actual. This is a comparison by type of service and tax identification number of actual penetration and savings versus the model. The user may view the PPO Configuration.

Figure 3D:
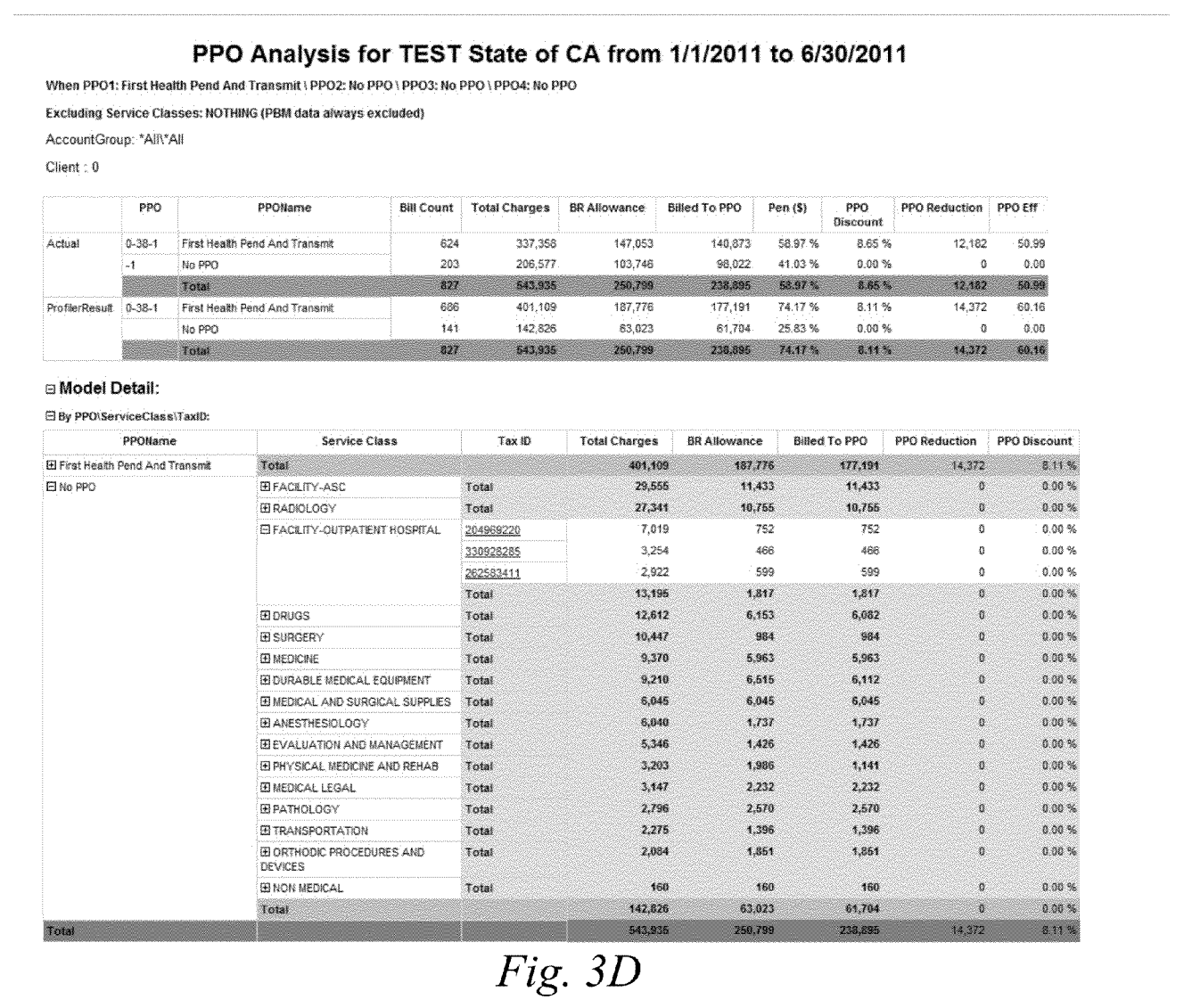

Referring now to FIG. 3D, an illustration of a results report based on "Model Detail By PPO\ServiceClass\TaxID", as described above, is shown. This is an interactive report allowing the user to select various views in real-time. The first table is a typical results report. The second table is a result report based on a plurality of parameters and a predetermined format. In this illustration, the user expanded the Model Detail field by selecting the "+" to the left of "Model Detail" to reveal a plurality of report options. The user then expanded the By PPO\ServiceClass\TaxID view option by selecting the "+" to the left of "By PPO\ServiceClass\TaxID" to reveal the results in this format. The first column in this results format is PPO network, the second column is Service Class, and the third column is Tax ID. The remaining columns are similar to a typical results report. The user can expand the No PPO field to reveal additional detail corresponding to No PPO. In this example, selecting this reveals a plurality of service classes for which no PPO network, including Facility-ASC, Radiology, Facility-Outpatient Hospital, Drugs, Surgery, Medicine, etc. The user may further analyze these results by service class. In this illustration, the user expanded "Facility-Outpatient Hospital" to view all the health care provider tax identification numbers associated with this PPO category and this Service Class category. In this illustration, there are three tax identification numbers. The remaining columns display results down to the level of granularity selected by the user.

Referring now to FIG. 3E, an illustration of a results view for "Other Pricing Hierarchy Match," as described above, is shown. The pricing hierarchy match is a summary showing the level of detail actually used by the model for each match in determining the estimated savings. After expanding the appropriate fields in this interactive report, the tool displays a table with a plurality of data. The first column is Pricing Hierarchy Match, the second column is Billed to PPO, and the third column is percent of total. In this example, the total amount billed to PPO is $177,191. The tool used two levels of data to match the bills to a model. The first level of detail is State-Net-ServiceClass-TaxID and accounts for $175,925, which is 99.29% of the total. This shows that for almost all of the billings, the information about the State the service was provided in, the network, the service class, and a corresponding tax identification number for the provider was used to by the model for each match in determining the estimated savings. The second level of detail is State-Net-ServiceClass and accounts for $1,266, which is 0.71% of the total. Similarly, this shows that for 0.71% of billings, the information about the State the service was provided in, the network, and the service class was used to by the model for each match in determining the estimated savings.

Figure 3F:
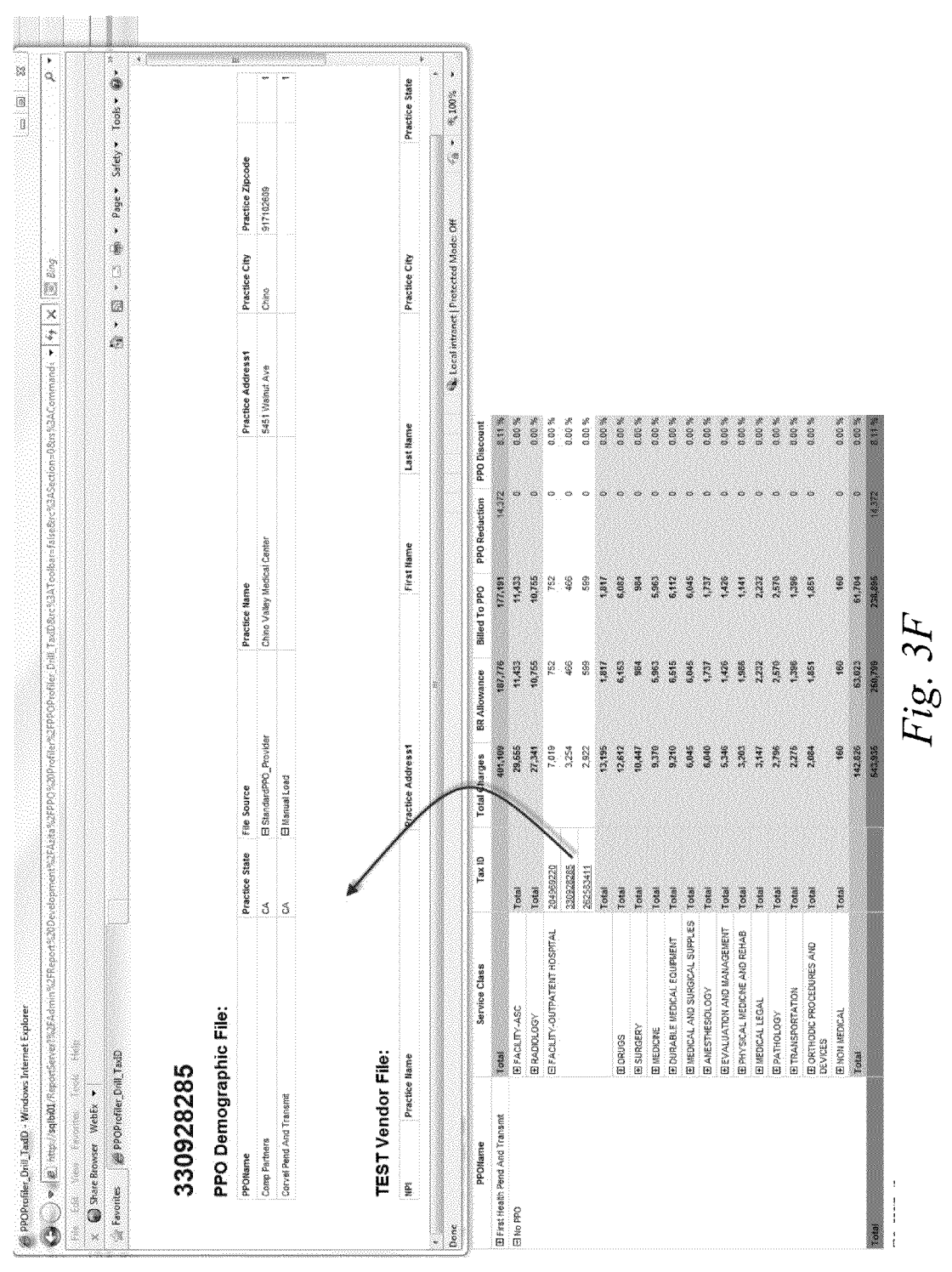

Referring now to FIG. 3F, an illustration of a PPO Demographic data (also referred to as Networks' Demographic Data 210 in FIG. 2A) is shown. The PPO Demographic data (above) is used by the tool to populate fields in the interactive results report (below). In this illustration, the user has expanded all the appropriate fields in order to reveal the tax identification number for a health care provider. This tax identification field may contain a uniform resource locator ("URL") to a web page hosted on a server containing demographic information about that health care provider. In this illustration, the user has selected demographic information for a health care provider whose tax identification number is 330928285. The demographic information includes the PPOs the provider is associated with, the practice state, the file source, the practice name, and the practice address.

Referring now to FIG. 3G, an illustration of optimizing network configuration is shown. In this example, the user has selected, via the user interface, four PPO networks for evaluation: BCC Pend and Transmit, IHP, PrimeHealth, and No PPO. The report shows the Actual results based on First Health Pend And Transmit PPO and No PPO. The report also shows the results based on the new configuration of networks. As illustrated in the report, the network optimization tool determined that the new configuration of PPO networks results in a 22.35 point increase in PPO efficiency, i.e., 73.34 for the new configuration and 50.99 for the old configuration. Using the new configuration, a client may save an additional $5,339.

Although the systems and methods of embodiments of the present solution may generally described in the context of PPO networks, these systems and methods may be used for any type and form of health care provider network. The network analyzer may be used any type of health care network, or any other type of network where bill review or similar data is available.

While the invention has been particularly shown and described with reference to specific embodiments, it should be understood by those skilled in the art that various changes in form and detail may be made therein without departing from the spirit and scope of the invention described in this disclosure.

What is claimed:

1. A method for evaluating efficiency of billing of services via a health care provider network, the method comprising:

(a) receiving, by a tool executing on a device, a first selection of a healthcare provider network from a plurality of health care provider networks;
(b) receiving, by the tool, a second selection of a state for which services were provided by the selected health care provider network; and
(c) determining, by the tool via a database of reviewed bill data, a penetration and a savings for bills on services within the state for the selected health care provider network, the tool determining the penetration as a total of bill reviewed charges billed to the selected health care provider network divided by a total of bill reviewed charges billed to a plurality of health care provider networks.

2. The method of claim 1, wherein step (a) further comprises receiving, by the tool, the selection of the healthcare provider network comprising a preferred provider organization (PPO).

3. The method of claim 1, wherein step (a) further comprises receiving, by the tool, identification of a time period for determining a penetration efficiency and savings.

4. The method of claim 3, wherein step (c) further comprises determining, by the tool, the penetration efficiency and the savings for bills on service within the state for the selected health care provider network during the time period.

5. The method of claim 1, wherein step (b) further comprises receiving, by the tool, the second selection of the state from a plurality of states in which the healthcare provider network provides services.

6. The method of claim 1, wherein step (a) further comprises receiving, by the tool, a third selection of a second health care provider network.

7. The method of claim 6, wherein step (c) further comprises determining, by the tool, the penetration and the savings for bills on service within the state for the second health care provider network.

8. The method of claim 1, wherein step (c) further comprises determining, by the tool, the savings by dividing a reduction for the selected health care provider by a total amount billed to the selected health care provider network.

9. The method of claim 1, wherein step (c) further comprises determining, by the tool, the penetration and the savings on a per service class basis for the selected health care provider network.

10. The method of claim 1, wherein step (c) further comprises determining, by the tool, the penetration and the savings on a per service class basis for the selected health care provider network and excluding one or more service classes selected from a plurality of service classes.

11. The method of claim 1, wherein step (c) further comprises determining, by the tool, a network efficiency based on the penetration and the savings.

12. A method for evaluating efficiency of selectable health care providers from a plurality of healthcare provider networks, the method comprising:
(a) receiving, by a tool executing on a device, a first selection of a first healthcare provider network of a plurality of healthcare provider networks;
(b) receiving, by the tool, a second selection of a second healthcare provider network of a plurality of healthcare provider networks;
(c) determining, by the tool, a penetration for each of the first healthcare provider network and the second healthcare provider network, the tool determining the penetration as a total of bill reviewed charges billed to a selected health care provider network divided by a total of bill reviewed charges billed to the plurality of healthcare provider networks; and
(d) comparing, by the tool, efficiency of billing of services between the first health care provider network and the second healthcare provider network, wherein the efficiency is calculated for each of the first healthcare provider network and the second healthcare provider network as a product of a corresponding reduction and penetration divided by 10.

13. The method of claim 12, wherein step (a) further comprises receiving, by the tool, a selection of a state from a plurality of states in which the first healthcare provider network provided services.

14. The method of claim 12, wherein step (a) further comprises receiving, by the tool, identification of a time period for the comparison.

15. The method of claim 12, wherein step (b) further comprises receiving, by the tool, the second selection of the second healthcare provider network of the plurality of healthcare provider networks for a same state as the first healthcare provider network.

16. The method of claim 12, wherein step (c) further comprises determining, by the tool from the database of reviewed bills, for each of the first healthcare provider network and the second healthcare provider network a network penetration and a network savings based on charges allowed via bill review.

17. The method of claim 12, wherein step (c) further comprises determining, by the tool from the database of reviewed bills, for each of the first healthcare provider network and the second healthcare provider network, the efficiency based on charges allowed via bill review.

18. The method of claim 12, further comprises receiving, by the tool, a selection of a client from a plurality of clients.

* * * * *